United States Patent [19]
Curran et al.

[11] Patent Number: 5,728,899
[45] Date of Patent: Mar. 17, 1998

[54] PREPARATION OF CIS-4-O-PROTECTED-2-CYCLOPENTENOL DERIVATIVES

[75] Inventors: Timothy T. Curran, Cincinnati, Ohio; David A. Hay, Indianapolis, Ind.; Jonathan C. Evans, Midland, Mich.

[73] Assignee: Hoechst Marion Roussel Inc., Cincinnati, Ohio

[21] Appl. No.: 588,584

[22] Filed: Feb. 1, 1996

Related U.S. Application Data

[63] Continuation-in-part of Ser. No. 411,136, Mar. 27, 1995, abandoned.

[51] Int. Cl.$^6$ ................................................. C07C 35/06
[52] U.S. Cl. ........................... 568/838; 568/731; 556/470; 556/482; 549/421
[58] Field of Search .......................... 549/421; 568/731, 568/838; 556/470, 482

[56] References Cited

U.S. PATENT DOCUMENTS 5,244,896  9/1993  Borcherding et al. .

OTHER PUBLICATIONS

C.R. Johnson, et al., J. Chem. Soc., Chem. Commun., 1139–1140 (1995).
S.M. Siddiqi, et al., Nucleosides & Nucleotides, 12(2)185–198, pp. 185–198, (1993).
Journal of the American Chemical Society, vol. 106, No. 6, 1750–1759 (1984).
Heterocycles, vol. 16, No. 4, 605–608 (1981).
Liebigs Annalen Der Chemie, No. 3, 195–200 (1991).
Tetrahedron, vol. 47, No. 36, 7569–7582, (1991).
Merlo, V., et al., J. Chem. Soc. Perkin Tans. 1, 1477 (1994).
Merlo, V., et al., J. Chem. Soc. Perkins Trans. 1, 1717, (1993).
H. C. Brown & P.M. Weissman, J. Am. Chem. Soc., 87(24), 5614 (1965).
K. Lauman & M. Schneider, Tetrahedron Lett. 25 (51), 5875 (1984).
Nokami, J., et al., Tetrahedron Lett., 32(21), 2409 (1991).
Harre, M., et al., Angew. Chem. Int. ed. Engl., 21, 480 (1982).
S. K. Hendrie & J.Leonard, Tetrahedron, 3289, (1987).
Corey, E.J., et al., Tetrahedron Lett., 27(20), 2199 (1986).
Nara, M., et al., Tetrahedron, 36, 3163 (1980).
Johnson C. R., et al., Tetrahedron Lett., 35(12), 1833 (1994).
M. Asami, Bull. Chem. Soc. Jpn., 63, 1402, (1990).
C. R. Johnson & S. J. Bis, Tetrahedron Lett., 33 (48), 7287 (1992).
M. Asami, Tetrahedron Lett., 26(47), 5803) (1985).

*Primary Examiner*—Amelia Owens
*Attorney, Agent, or Firm*—Nelsen L. Lentz

[57] ABSTRACT

The present invention relates to a novel process for preparing cis-4-O-protected-substituted-2-cyclopentenol derivatives comprising, a) dissolving a 4-O-protected-2-cyclopentenone in a suitable organic solvent; and b) treating the solution with a suitable Lewis acid and a suitable reducing agent at a temperature of from about −100° C. to about 20° C. The cis-4-O-protected-substituted-2-cyclopentenol derivatives are useful intermediates in the preparation of various cyclopentanyl and cyclopentenyl purine analogs which are useful as immunosuppressants and in the preparation of various prostaglandins.

12 Claims, No Drawings

PREPARATION OF CIS-4-O-PROTECTED-2-CYCLOPENTENOL DERIVATIVES

This application is a CIP of Ser. No. 08/411,136 filed Mar. 27, 1995, now abandoned.

BACKGROUND OF THE INVENTION

The present invention relates to a novel process for preparing cis-4-O-protected-2-cyclopentenol derivatives which are useful intermediates in the preparation of various cyclopentanyl and cyclopentenyl purine analogs which are useful as immunosuppressants as disclosed by Borcherding, et al. in European Patent Application Publication Nos. 0 475 411 A1, published Mar. 18, 1992, 475 413 A2, published Mar. 18, 1992, and 0 545 413 A1, published Jun. 9, 1993. In addition, cis-4-O-protected-2-cyclopentenol derivatives are useful intermediates in the preparation of various prostaglandins.

SUMMARY OF THE INVENTION

The present invention provides a novel process for the preparation of a CIS compound of the formula (II):

formula (II)

wherein Pg is selected from the group consisting of benzyl, substituted benzyl, —$CH_2OCH_3$, —$CH_2SCH_3$, —$CH_2OCH_2$phenyl, —$CH_2OCH_2CH_2OCH_3$, —$CH_2OCH_2CCl_3$, —$CH(OCH_2CH_2Cl)_2$, —$CH_2OCH_2CH_2Si(CH_3)_3$, —$CH(OC_2H_5)CH_3$, —$C(OCH_3)(CH_3)_2$, —$CH(CH_3)OCH(CH_3)_2$, —$CH_2CCl_3$, —$C(CH_3)_3$, —$CH_2CH=CH_2$, —$CH_2CH=CH$phenyl, —$CH(phenyl)_2$, —$C(phenyl)_3$, tetrahydropyranyl, 4-methoxytetrahydropyranyl, 3-bromotetrahydropyranyl, tetrahydrothiopyranyl, 4-methoxytetrahydrothiopyranyl, tetrahydrofuranyl, tetrahydrothiofuranyl, and $SiR_1R_2R_3$, wherein $R_1$, $R_2$ and $R_3$ are each independently $C_1$–$C_4$ alkyl, phenyl, benzyl, substituted phenyl or substituted benzyl, comprising;

a) dissolving a compound of the formula (I)

formula (I)

wherein Pg is defined as above, in a suitable organic solvent; and b) treating the solution with a suitable Lewis acid and a suitable reducing agent at a temperature of from about −100° C. to about 20° C.

The present invention further provides a novel process for the preparation of the CIS enantiomer of the formula (IIa):

formula (IIa)

wherein Pg is selected from the group consisting of benzyl, substituted benzyl, —$CH_2OCH_3$, —$CH_2SCH_3$, —$CH_2OCH_2$phenyl, —$CH_2OCH_2CH_2OCH_3$, —$CH_2OCH_2CCl_3$, —$CH(OCH_2CH_2Cl)_2$, —$CH_2OCH_2CH_2Si(CH_3)_3$, —$CH(OC_2H_5)CH_3$, —$C(OCH_3)(CH_3)_2$, —$CH(CH_3)OCH(CH_3)_2$, —$CH_2CCl_3$, —$C(CH_3)_3$, —$CH_2CH=CH_2$, —$CH_2CH=CH$phenyl, —$CH(phenyl)_2$, —$C(phenyl)_3$, tetrahydropyranyl, 4-methoxytetrahydropyranyl, 3-bromotetrahydropyranyl, tetrahydrothiopyranyl, 4-methoxytetrahydrothiopyranyl, tetrahydrofuranyl, tetrahydrothiofuranyl, and $SiR_1R_2R_3$, wherein $R_1$, $R_2$ and $R_3$ are each independently $C_1$–$C_4$ alkyl, phenyl, benzyl, substituted phenyl or substituted benzyl, comprising;

a) dissolving an enantiomeric compound of the formula (Ia)

formula (Ia)

wherein Pg is defined as above, in a suitable organic solvent; and b) treating the solution with a suitable Lewis acid and a suitable reducing agent at a temperature of from about −100° C. to about 20° C.

In addition, the present invention provides a novel process for the preparation of the CIS enantiomer of the formula (IIb):

formula (IIb)

wherein Pg is selected from the group consisting of benzyl, substituted benzyl, —$CH_2OCH_3$, —$CH_2SCH_3$, —$CH_2OCH_2$phenyl, —$CH_2OCH_2CH_2OCH_3$, —$OCH_2OCH_2CCl_3$, —$CH(OCH_2CH_2Cl)_2$, —$CH_2OCH_2CH_2Si(CH_3)_3$, —$CH(OC_2H_5)CH_3$, —$C(OCH_3)(CH_3)_2$, —$CH(CH_3)OCH(CH_3)_2$, —$CH_2CCl_3$, —$C(CH_3)_3$, —$CH_2CH=CH_2$, —$CH_2CH=CH$phenyl, —$CH(phenyl)_2$, —$C(phenyl)_3$, tetrahydropyranyl, 4-methoxytetrahydropyranyl, 3-bromotetrahydropyranyl, tetrahydrothiopyranyl, 4-methoxytetrahydrothiopyranyl, tetrahydrofuranyl, tetrahydrothiofuranyl, and $SiR_1R_2R_3$, wherein $R_1$, $R_2$ and $R_3$ are each independently $C_1$–$C_4$ alkyl, phenyl, benzyl, substituted phenyl or substituted benzyl, comprising;

a) dissolving an enantiomeric compound of the formula (Ib)

formula (Ib)

wherein Pg is defined as above, in a suitable organic solvent; and b) treating the solution with a suitable Lewis acid and a suitable reducing agent at a temperature of from about −100° C. to about 20° C.

In addition, the present invention further provides a novel process for the preparation of the CIS compounds of the formulas (IIb) and (IV):

formula (IIb)

formula (IV)

wherein Z is $C_2$–$C_4$ alkanoyl; and Pg is selected from the group consisting of benzyl, substituted benzyl, —$CH_2OCH_3$, —$CH_2SCH_3$, —$CH_2OCH_2$phenyl, —$CH_2OCH_2CH_2OCH_3$, —$CH_2OCH_2CCl_3$, —$CH(OCH_2CH_2Cl)_2$, —$CH_2OCH_2CH_2Si(CH_3)_3$, —$CH(OC_2H_5)CH_3$, —$C(OCH_3)(CH_3)_2$, —$CH(CH_3)OCH(CH_3)_2$, —$CH_2CCl_3$, —$C(CH_3)_3$, —$CH_2CH=CH_2$, —CH₂CH=CHphenyl, —CH(phenyl)₂, tetrahydropyranyl, 4-methoxytetrahydropyranyl, 3-bromotetrahydropyranyl, tetrahydrothiopyranyl, 4-methoxytetrahydrothiopyranyl, tetrahydrofuranyl, tetrahydrothiofuranyl, and SiR₁R₂R₃, wherein R₁, R₂ and R₃ are each independently C₁–C₄ alkyl, phenyl, benzyl, substituted phenyl or substituted benzyl, comprising;

a) dissolving a compound of the formula (I)

formula (I)

wherein Pg is defined as above, in a suitable organic solvent;

b) treating the solution with a suitable Lewis acid and a suitable reducing agent at a temperature of from about −100° C. to about 20° C. to yield the CIS compound of formula (II);

formula (II)

wherein Pg is as defined above;

c) treating the CIS compound of formula (II) with a suitable enzyme and an excess of a suitable acylating agent, in a suitable solvent to yield a mixture of compounds of the formulas (IIb) and (IV), as defined above; and d) separating the compound of formula (IIb) from compound of formula (IV).

The invention further provides a novel process for the preparation of a CIS compound of formulas (II), (IIa), (IIb) or (IV), as defined above, wherein a suitable alcohol is added to the reaction mixture concomitantly with or prior to treating the compound of formula (I) with the suitable reducing agent.

The invention further provides a novel process for the preparation of the CIS compounds of the formulas (VIb) and (VII):

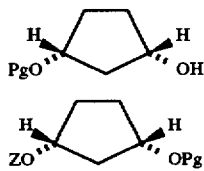

formula (VIb)

formula (VII)

wherein Z is C₂–C₄ alkanoyl and Pg is selected from the group consisting of benzyl, substituted benzyl, —CH₂OCH₃, —CH₂SCH₃, —CH₂CH₂phenyl, —CH₂OCH₂CH₂OCH₃, —CH₂OCH₂CCl₃, —CH(OCH₂CH₂Cl)₂, —CH₂OCH₂CH₂Si(CH₃)₃, —CH(OC₂H₅)CH₃, —C(OCH₃)(CH₃)₂, —CH(CH₃)OCH(CH₃)₂, —CH₂CCl₃, —C(CH₃)₃, —CH₂CH=CH₂, —CH₂CH=CHphenyl, —CH(phenyl)₂, tetrahydropyranyl, 4-methoxytetrahydropyranyl, 3-bromotetrahydropyranyl, tetrahydrothiopyranyl, 4-methoxytetrahydrothiopyranyl, tetrahydrofuranyl, tetrahydrothiofuranyl,and SiR₁R₂R₃, wherein R₁, R₂ and R₃ are each independently C₁–C₄ alkyl, phenyl, benzyl, substituted phenyl or substituted benzyl, comprising treating the CIS compound of formula (VI);

formula (VI)

wherein Pg as as defined above, with a suitable enzyme and an excess of a suitable acylating agent in a suitable solvent, to yield a mixture of compounds of the formulas (VIb) and (VII), as defined above; and f) separating the compound of formula (VIb) from the compound of formula (VII).

DETAILED DESCRIPTION OF THE INVENTION

The term "stereoisomers" is a general term for all isomers of individual molecules that differ only in the orientation of their atoms in space. It includes geometric (cis/trans) isomers, and isomers of compounds with more than one asymmetric center that are not mirror images of one another (diastereomers). The terms "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction. The terms "racemic mixture" or "racemic modification" refer to a mixture of equal parts of enantiomers. A racemic modification or racemic mixture are optically inactive. As used herein the prefixes "(+)" and "(−)" are employed to designate the sign of rotation of plane polarized light by the compound, with (+) meaning the compound is dextrorotatory and (−) meaning the compound is levorotatory.

The term "enantiomeric enrichment" refers to the increase in the amount of one enantiomer as compared to the other enantiomer. A convenient method of expressing enantiomeric enrichment achieved is the concept of "enantiomeric excess" or "ee", which is expressed by the following equation;

$$ee = \frac{E^1 - E^2}{E^1 + E^2} \times 100$$

in which $E^1$ is the amount of the first enantiomer and $E^2$ is the amount of the second corresponding enantiomer. For example, where the initial ratio of two enantiomers in a reaction is 50:50 (a racemic mixture) and the reaction produces enantiomeric enrichment with a final ratio of 90:10, then the ee with respect to the first enantiomer is 80%. It is preferred that ee's of greater than 90% be obtained.

It is understood that the enantiomers of formula (IIa) and the corresponding enantiomers of formula (IIb) are mirror images of each other. It is further understood that the enantiomers of formulas (IIa) and (IIb) are also in the CIS configuration. In addition, the CIS compounds of formula (II) are racemic mixtures of the corresponding enantiomers of formulas (IIa) and (IIb). It is also further understood that the enantiomeric compounds of formula (Ia) and the corresponding enantiomeric compounds of formula (Ib) are mirror images of each other. For example the enantiomer of formula (Ia') and the enantiomer of formula (Ib') below are mirror images of each other.

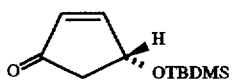

formula (Ia')

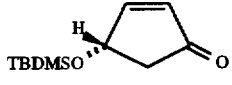

formula (Ib')

As used herein the term "C₁–C₄ alkyl" refers to a saturated straight or branched chain hydrocarbon radical of one to four carbon atoms. Included within the scope of this term are methyl, ethyl, n-propyl, isopropyl, n-butyl, isobutyl and the like.

As used herein the term "C$_2$–C$_4$ alkanoyl" refers to an acetyl, propionyl and butyryl group.

As used herein the term "C$_1$–C$_4$ alkoxy" refers to a straight or branched alkoxy group containing from 1–4 carbon atoms and includes methoxy, ethoxy, n-propoxy, isopropoxy, n-butoxy, isobutoxy, t-butoxy, and the like. As used herein the term "halogen", "halo", "halide", "hal" refers to fluorine atom, chlorine atom, bromine atom, or iodine atom.

The term "TBDMS" refers to a tert-butyldimethylsilyl functionality of the formula:

$$\begin{array}{c}\text{CH}_3 \quad \text{CH}_3 \\ | \quad\quad | \\ -\text{Si}-\text{C}-\text{CH}_3 \\ | \quad\quad | \\ \text{CH}_3 \quad \text{CH}_3\end{array}$$

The term "phenyl" refers the phenyl functionality of the formula:

The terms "benzyl" or "Bn" refers the benzyl functionality of the formula:

The term "substituted phenyl" refers the substituted phenyl functionality of the formula:

wherein R is C$_1$–C$_4$ alkyl, C$_1$–C$_4$ alkoxy, NO$_2$, —CN, F, Cl, Br or I, which can be located at the ortho, meta or para position on the ring.

The term "substituted benzyl" refers the substituted benzyl functionality of the formula:

wherein R is C$_1$–C$_4$ alkyl, C$_1$–C$_4$ alkoxy, NO$_2$, —CN, F, Cl, Br or I, which can be located at the ortho, meta or para position on the ring.

The term "THP" refers the tetrahydro-pyran-2-yl functionality of the formula:

The terms "acetyl", "propionyl" and "butyryl" refer the following functional groups respectively:

As used herein a CIS compound such as compound A means the hydrogens at positions 1 and 2 on the cyclopentenyl ring are both on the same plane of the ring and the substituents OH and OJ, wherein J is H or Pg, at positions 1 and 2, are also on the same plane of the ring as each other. Thus, OH and OJ are in the plane opposite the hydrogens at positions 1 and 2.

The designation "—■" refers to a bond that protrudes forward out of the plane of the page.

The designation "⋯⋯" refers to a bond that protrudes backward out of the plane of the page.

The designation "⁓" refers to a bond for which the stereochemistry is not designated.

U.S. patent application Ser. No. 08/411,136 filed Mar. 27, 1995, entitled "PREPARATION OF CIS-4-O-PROTECTED-2-CYCLOPENTENOL DERIVATIVES" is hereby incorporated by reference.

Scheme I describes the preparation of compounds of formulas (I), (II) and (III). All the substituents, unless otherwise indicated, are previously defined. The reagents and starting materials are readily available to one of ordinary skill in the art.

Scheme I

-continued
Scheme I

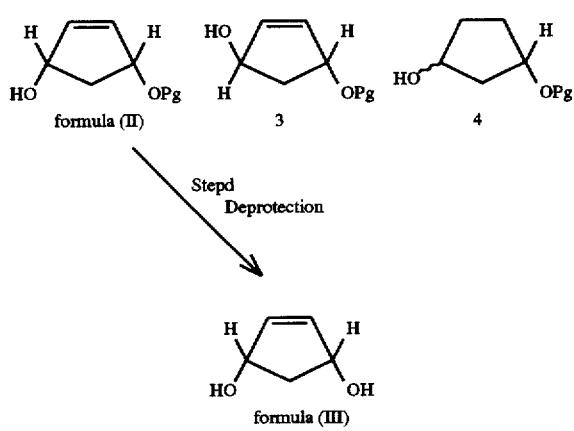

formula (II)    3    4

Step d
Deprotection formula (III)

In step a, the 4-hydroxy-2-cyclopentenone (2) is readily prepared from furfuryl alcohol (1) by one of ordinary skill in the art following the procedure described by Masayoshi Nanni, Harima Ta-machi and Moriyama-shi, Japanese Patent Disclosure Bulletin, KOKAI No. 57-62236, Apr. 15, 1982, or alternatively as described by G. Piancatelli et al., *Tetrahedron*, 34, 2775 (1978).

In step b, 4-hydroxy-2-cyclopentenone (2) is protected with a suitable protecting group to provide the compound of formula (I) utilizing techniques and procedures well known to one of ordinary skill in the art. Examples of suitable protecting groups are described by T. W. Greene, *"Protective Groups in Organic Synthesis"*, John Wiley & Sons, Inc., 1981, Chapter 2, such as methoxymethyl, methylthiomethyl, benzyloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, 2,2,2-trichloroethyl, tert-butyl, allyl, cinnamyl, p-chlorophenyl, benzyl, p-methoxybenzyl, o-nitrobenzyl, p-nitrobenzyl, p-chlorobenzyl, p-bromobenzyl, p-cyanobenzyl, diphenylmethyl, triphenylmethyl triethylsilyl, triisopropylsilyl, isopropyldimethylsilyl, tert-butyldimethylsilyl, methyldiethylsilyl, dimethylethylsilyl, methyldiisopropylsilyl, methyl-di-tert-butylsilyl, tribenzylsilyl, triphenylsilyl, phenyldimethylsilyl, benzylmethylethylsilyl, phenylethylmethylsilyl, tri-o-tolylsilyl, tert-butyldiphenylsilyl and the like. The preferred suitable protecting groups are tetrahydropyranyl and tert-butyldimethylsilyl. The most preferred suitable protecting groups are tert-butyldimethylsilyl and trityl. The compounds of formula (I) are readily prepared by one of ordinary skill utilizing generally the procedures described by T. W. Greene, *"Protective Groups in Organic Synthesis"*, John Wiley & Sons, Inc., 1981, Chapter 2. For example, the protection step can be carried out by dissolving the 4-hydroxy-2-cyclopentenone (2) in an inert, substantially anhydrous, organic solvent in the presence of an acid acceptor, preferably a nitrogen base such as triethylamine, quinoline, lutidine, imidazole or pyridine. The preferred acid acceptor is triethylamine. Examples of suitable solvents for the protection step are methylene chloride, tetrahydrofuran, chloroform, tetrachloroethane, nitromethane, benzene, diethyl ether, acetonitrile, dimethylformamide and the like.

The preferred suitable solvent is tetrahydrofuran. A catalytic amount of 4-dimethylaminopyridine (DMAP) may optionally be added to the solution. The solution is then cooled to about 0° C and approximately one equivalent of a suitable silylating agent is added to the solution. The reaction is allowed to stir for 2 to 14 hours and then the compound of formula (I) is isolated and purified by techniques well known in the art, such as extractive methods and distillation. For example, the reaction is poured into aqueous 0.5N hydrochloric acid and the phases separated. The aqueous phase is extracted with a suitable organic solvent, such as heptane. The organic extract is combined with the organic phase and rinsed with 5% sodium bicarbonate, brine, dried over anhydrous magnesium sulfate, filtered and concentrated under vacuum. The residue can then be purified by Kugelrohr distillation to provide the compound of formula (I).

In step c, the compound of formula (I) is selectively reduced to provide the CIS compound of formula (II). For example, the compound of formula (I) and a suitable Lewis acid are dissolved in a suitable organic solvent under an inert atmosphere, such as argon, with stirring. The suitable organic solvent is essentially anhydrous and may be a mixture of suitable organic solvents or a single organic solvent. Examples of a suitable organic solvent are diethyl ether, dipropyl ether, tert-butyl methyl ether, toluene/tert-butyl methyl ether, heptane/tert-butyl methyl ether, toluene/diethyl ether and the like. The preferred suitable organic solvents are diethyl ether, toluene/diethyl ether or toluene/tert-butyl methyl ether. The most preferred suitable organic solvents are toluene/diethyl ether or toluene/tert-butyl methyl ether. The amount of suitable Lewis acid utilized is from about 0.10 eq to about 5 eq with about 0.5 eq being preferred. Examples of a suitable Lewis acid are lithium chloride, lithium bromide, lithium iodide, lithium perchlorate, zinc chloride, magnesium bromide, cerium(III) chloride and the like. The preferred suitable Lewis acids are lithium iodide and lithium bromide, with lithium iodide being the most preferred suitable Lewis acid. The temperature of the solution required for the selective reduction is from about −100° C. to about 20° C. The preferred temperature is from about −78° C. to about −10° C. with about −25° C. being the most preferred temperature of the solution. The solution is then treated with a suitable reducing agent. The preferred amount of suitable reducing agent utilized is from about 0.4 eq to about 5 eq, with about 0.5 eq being most preferred. Examples of suitable reducing agents are lithium aluminum hydride, lithium trimethoxyaluminumhydride, 65+wt. % solution of sodium bis(2-methoxyethoxy)aluminum hydride in toluene (also known as REDAL®) (Aldrich Chemical Company, Milwaukee, Wis.), lithium borohydride and the like. The preferred suitable reducing agent is lithium aluminum hydride. After addition of the suitable reducing agent, the reaction is stirred for about 1 hour to about 5 hours, with about 2 hours being preferred. The reaction is then cautiously quenched and the product isolated and purified utilizing conditions well known in the art. For example, approximately 1 to 2 eq of aqueous sodium hydroxide (1N) is added at a rate that maintains the temperature of the reaction below 20° C. After the reaction is quenched, it is filtered through a pad of diatomaceous earth, such as CELITE, (available from Aldrich Chemical Company, Milwaukee, Wis.). The pad of diatomaceous earth is then rinsed with a suitable organic solvent, such as toluene. The filtrate is separated and the aqueous phase is extracted with a suitable solvent, such as toluene. The organic phases can be combined and washed sequentially with aqueous sodium hydroxide (1N), brine, dried over anhydrous magnesium sulfate, filtered and concentrated under vacuum to provide the compound of formula (II), which can be purified by techniques well known in the art, such as chromatography or distillation. Gas chromatography (GC) can be utilized by one of ordinary skill in the art to determine the ratio of CIS compound of formula (II) to the by-products of the reduction, which are compounds 2 and 3.

In addition, in step c, the compound of formula (I) can be selectively reduced to provide the CIS compound of formula (II) by addition of a suitable alcohol to the reaction mixture described above, under conditions analogous to those described hereinabove, either in the presence of the suitable Lewis acid, or alternatively, without addition of the suitable Lewis acid. Examples of suitable alcohols are isopropanol, 2-methyl-1-propanol, 2-methyl-2-butanol, 2-methyl-1-butanol, 3-methyl-1-butanol, 3-methyl-2-butanol, triethylsilanol, tert-butyldimethylsilanol, methyldiisopropylsilanol, isopropyldimethylsilanol, triisopropylsilanol, methyl-di-tert-butylsilanol, tribenzylsilanol, triphenylsilanol, tert-butyldiphenylsilanol, phenyldimethylsilanol, benzylmethylethylsilanol, phenylmethylethylsilanol, tri-o-tolylsilanol, phenol and the like. The preferred suitable alcohols are isopropanol and tert-butyldimethylsilanol with tert-butyldimethylsilanol being most preferred. The amount of alcohol added can range from about 0 mol % to about 100 mol %. The preferred amount of alcohol added is about 16 mol % to about 30 mol % with about 20 mol % being most preferred. More specifically, for example, a suitable reducing agent, such as lithium aluminum hydride is combined with a suitable Lewis acid, such as lithium iodide in a suitable organic solvent, such as toluene. The reaction mixture is cooled to about −40° C. to about −20° C. and a mixture of a compound of formula (I), such as 4-tert-butyldimethylsiloxy-3-cyclopentanone, tert-butyldimethylsilanol and tert-butyl methyl ether is added slowly to the reaction mixture. After stirring for about 4 hours the reaction is quenched with aqueous ammonium chloride and the product isolated and purified by techniques well known in the art, such as column chromatography on silica gel or by vacuum distillation.

It is understood by one of ordinary skill in the art that the reagents may be combined in various manners so long as the suitable alcohol is present when the suitable reducing agent is combined with the compound of formula (I). For example, the suitable Lewis acid can be combined with the suitable reducing agent and suitable alcohol in a suitable organic solvent, such as toluene. The reaction mixture is then treated with a solution of a compound of formula (I) in a suitable organic solvent, such as tert-butyl methyl ether to provide the CIS compound of formula (II). In another example, the suitable Lewis acid can be combined with the suitable reducing agent, a suitable alcohol in a suitable organic solvent, such as toluene, and a compound of formula (I) followed by addition of a suitable organic solvent, such as tert-butyl methyl ether to provide the CIS compound of formula (II).

In step d, the CIS compound of formula (II) is deprotected under conditions well known in the art to provide the CIS compound of formula (III) [see for example T. W. Greene, "Protective Groups in Organic Synthesis", John Wiley & Sons, Inc., 1981, Chapter 2]. For example, the compound of formula (II), wherein Pg is a trialkylsilyl protecting group, such as a tert-butyldimethylsilyl group, is dissolved in a suitable organic solvent, such as tetrahydrofuran. It is then optionally treated with approximately 0.15 eq of a suitable amine, such as triethylamine followed by treatment with approximately 1.1 eq of tetrabutylammonium fluoride (as a 1N solution in tetrahydrofuran) at room temperature. The reaction is stirred for about 2 to 6 hours and then the product is isolated and purified by techniques well known in the art. For example, the reaction is concentrated under vacuum and the residue purified by flash chromatography on silica gel with a suitable eluent, such as 10% acetone/ethyl acetate. The purified material is then recrystallized from a suitable organic solvent, such as chloroform to provide cis-2-cyclopentenyl-1,4-diol of formula (III).

In addition, in step d, the compound of formula (II) wherein Pg is a tetrahydro-pyran-2-yl group is dissolved in a suitable organic solvent, such as methanol or ethanol, and treated with a suitable acid, such as pyridinium p-toluenesulfonate (PPTS), at room temperature for 1 to 4 hours. The product is isolated and purified by techniques well known in the art. For example, the reaction is neutralized with a suitable base, such as sodium bicarbonate and concentrated under vacuum. The residue is then purified by flash chromatography on silica gel with a suitable eluent, such as 10% acetone/ethyl acetate. The purified material is then recrystallized from a suitable organic solvent, such as chloroform to provide cis-2-cyclopentenyl-1,4-diol of formula (III).

In a manner analogous to that described in Scheme I, compounds of formulas (IIa) and (IIb) can be prepared from the corresponding compounds of formulas (Ia) and (Ib). The compounds of formulas (Ia) and (Ib) can be prepared by one of ordinary skill in the art, for example following generally the procedure described by M. Asami, *Tetrahedron Letters*, 26(47), 5803–5806 (1985) or S. P. Khanapure et al., *J. Org. Chem.*, 60, 7548–7551 (1995). In addition, the compounds of formulas (Ia) and (Ib) can be prepared by one of ordinary skill in the art from the compounds of formulas (IIb) and (IV) prepared in Scheme II shown below.

Scheme II describes the preparation of compounds of formulas (IIb) and (IV) from compounds of formula (II). Compounds of formula (II) can be prepared following the procedure set forth in Scheme I. In addition, compounds of formula (II) can be prepared by converting cyclopentadiene to cis-2-cyclopentenyl-1,4-diol following the procedure described by Kaneko, C., et al., *Synthesis*, 876, (1974), and then monoprotecting the diol with a suitable protecting group under conditions well known to one of ordinary skill in the art, for example as described by Jain, S., et al., *Chemistry and Industry*, 17, 576, (September 1990), Rapoport, H. and Castello, A., *J. Org. Chem.*, 51, 1006 (1986), McDougal, P., et al., *J. Org. Chem.*, 51, 3388 (1986) and Roush, et al., *J. Org. Chem.*, 56, 1636 (1991). All the substituents, unless otherwise indicated, are previously defined. The reagents and starting materials are readily available to one of ordinary skill in the art.

Scheme II

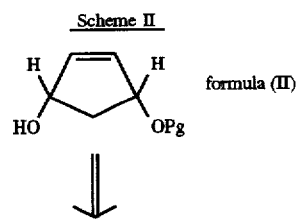

formula (II)

-continued
Scheme II

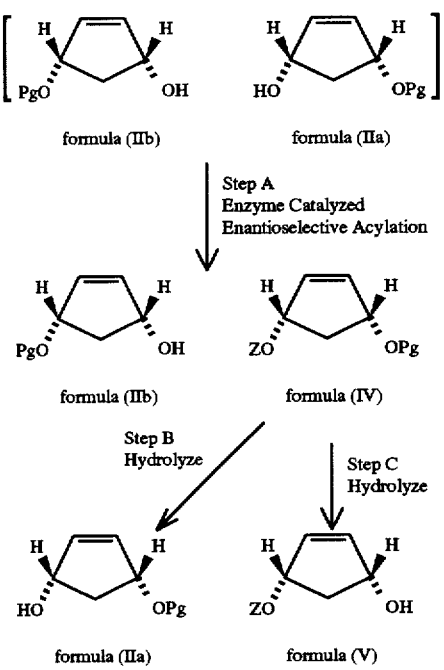

In Scheme II, step A, a compound of formula (II) is subjected to an enzyme catalyzed enantioselective acylation reaction under analogous conditions well known in the art, such as that described by Johnson, C. R., et al., *Tetrahedron Letters*, 35(12), 1833–1834 (1994), C. R. Johnson and S. J. Bis, *Tetrahedron Letters*, 33(48), 7287–7290 (1992), Theil, et al., *Liebiegs Ann. Chem.*, 195–200 (1991), Theil, et al., *Tetrahedron*, 47(36), 7569–7582 (1991) and Theil, et al., *Synthesis*, 540 (1988), to provide the compounds of formula (IIb) and (IV).

For example, a compound of formula (II) is dissolved in a suitable solvent or solvent mixture, such as tert-butyl methyl ether, diethyl ether, diisopropyl ether, tetrahydrofuran, cyclohexane, toluene, hexane and the like. The preferred suitable solvents are tert-butyl methyl ether and cyclohexane. The solution is treated with a suitable enzyme and an excess of a suitable acylating agent. Examples of suitable acylating agents are isopropenyl acetate, isopropenyl propionate, isopropenyl butyrate, vinyl acetate, vinyl propionate, vinyl butyrate and the like. The preferred suitable acylating agent is vinyl acetate. About 0.70 equivalents of an alkyl amine, such as triethylamine, may be optionally added, with stirring, at a temperature of about 15° C. to about 55° C. A suitable enzyme is an enzyme that catalyzes the enantioselective acylation of the compound of formula (II) whereby essentially only a single enantiomer of the racemic mixture, such as the compound of formula (IIa), is acylated under the described conditions to produce a mixture of compounds of formula (IV) and of formula (IIb), wherein Z is acetyl, propionyl or butyryl. Examples of suitable enzymes are pancreatin (available from Sigma Chemical Company), Candida antarctica lipase B (Novo Nordisk SP 435), lipozyme IM (available from Novo Nordisk) and the like. The preferred suitable enzyme is pancreatin. The preferred temperature is 22° C. The reaction is then stirred for about 6 hours to 24 hours, preferably about 8 hours. The reaction is then filtered through diatomaceous earth and the filtrate is concentrated under vacuum to provide a mixture of compounds of formula (IIb) and (IV). The resulting mixture of compounds of formula (IIb) and (IV) are readily separated from one another by techniques and procedures well known to one of ordinary skill in the art, such as chromatography or distillation. For example, the mixture can be chromatographed on silica gel with a suitable eluent, such as ethyl acetate/hexane to provide a clean separation of compounds of formula (IIb) from compounds of formula (IV).

In Scheme II, step B, the compounds of formula (IV) can be selectively hydrolyzed by procedures well known to one of ordinary skill in the art to produce the compounds of formula (IIa). For example, the compound of formula (IV) wherein Pg is a tetrahydro-pyran-2-yl protecting group, or a trialkylsilyl protecting group, such as a tert-butyldimethylsilyl group, can be dissolved in a suitable solvent or solvent mixture, such as THF/methanol/water, and treated with one equivalent of a suitable base, such as lithium hydroxide monohydrate. The reaction is stirred at room temperature for about 1 to 8 hours and the product is then isolated and purified by techniques well known in the art, such as extractive methods and chromatography. For example, the reaction is diluted with a suitable organic solvent, such as diethyl ether, rinsed with water, dried over anhydrous magnesium sulfate, filtered and concentrated under vacuum. The residue is then purified by chromatography on silica gel with a suitable eluent, such as ethyl acetate/hexane, to provide the compound of formula (IIa).

In Scheme II, step C, the compounds of formula (IV) can be selectively hydrolyzed by procedures well known to one of ordinary skill in the art to produce compounds of formula (V). For example, the compound of formula (IV) wherein Pg is a tetrahydro-pyran-2-yl protecting group can be dissolved in a suitable organic solvent such as ethanol, and treated with p-toluenesulfonic acid. In addition, the compound wherein Pg is a tert-butyldimethylsilyl group on formula (IV), can be dissolved in a suitable organic solvent, such as tetrahydrofuran, and treated with n-tetrabutylammonium fluoride. Either reaction is then stirred at room temperature for about 1 to 8 hours and the product is then isolated and purified by techniques well known in the art, such as extractive methods and chromatography. For example, either reaction is diluted with a suitable organic solvent, such as diethyl ether, rinsed with water, dried over anhydrous magnesium sulfate, filtered and concentrated under vacuum. The residue is then purified by chromatography on silica gel with a suitable eluent, such as ethyl acetate/hexane, to provide the compound of formula (V).

The compounds of formulas (IIb) and (IIa) can then be readily converted to the corresponding enantiomers of O-protected 4-hydroxy-2-cyclopentenone by procedures known to one of ordinary skill in the art. For example, the procedures described by M. Asami, *Tetrahedron Letters*, 26(47), 5803–5806 (1985), K. Laumen and M Schneider, *Tetrahedron Letters*, 25(51), 5875–5878 (1984), M. Nara et al., *Tetrahedron*, 36, 3161–3170 (1980) and J. Nokami, et al., *Tetrahedron Letters*, 32(21), 2409–2412 (1991), can be followed in an analogous manner to produce both enantiomers of O-protected-4-hydroxy-2-cyclopentenone. For example, the compound of formulas (IIa) or (IIb) is dissolved in a suitable organic solvent, such as methylene chloride and treated with a suitable oxidizing agent, such as manganese dioxide ($MnO_2$), pyridinium dichromate (PDC) or pyridinium chlorochromate (PCC) to provide the ketones of formulas (Ia) and (Ib). The compounds of formulas (IIa) and (IIb) are useful synthetic intermediates for the enantioselective synthesis of prostaglandins, for example see M. Asami, *Tetrahedron Letters*, 26(47), 5803–5806 (1985). In addition, the enantiomers of formulas (Ia) and (Ib) can be prepared in general following the procedure of Corey, E. J., et al., *Tetrahedron Letters*, 27, 2199 (1986) or S. P. Khanapure et al., *J. Org. Chem.*, 60, 7548–7551 (1995).

Compounds of the formulas (VIa), (VIb), (VII) and (VIII) can be prepared as described in Scheme III. All the substituents, unless otherwise indicated, are previously defined. The reagents and starting materials are readily available to one of ordinary skill in the art.

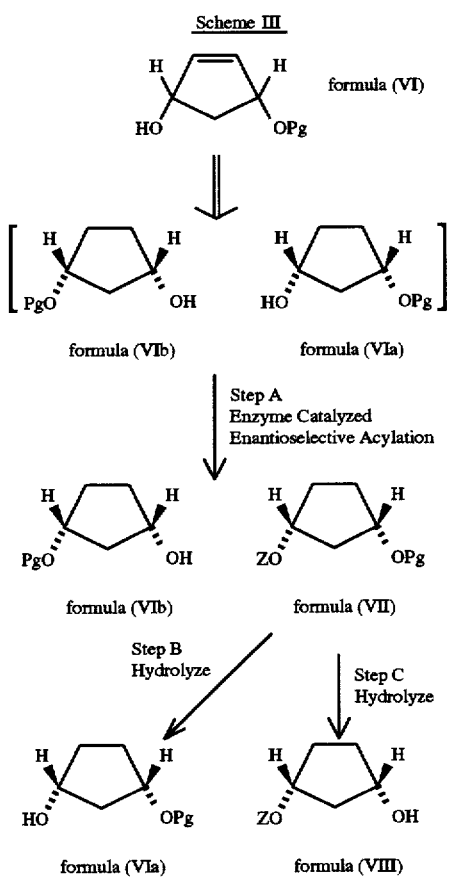

In Scheme III the compound of formula (VI) is prepared by one of ordinary skill in the art, for example, by reduction of the double bond in the compound of formula (II). More specifically, the compound of formula (II) is combined with Ni₂B in a suitable organic solvent, such as methanol and the reaction mixture is stirred for about 15–20 hours at room temperature under an atmosphere of hydrogen. The product is then isolated and purified by techniques and procedures well known in the art. For example, the hydrogen atmosphere is purged with nitrogen, the reaction mixture is filtered through diatomaceous earth, the solids washed with methanol and the filtrate concentrated under vacuum. The residue can then be purified by column chromatography or vacuum distillation to provide the purified compound of formula (VI).

In Scheme III, step A, the compound of formula (VI) is subjected to an enzyme catalyzed enantioselective acylation reaction under analogous conditions well known in the art, such as that described by Johnson, C. R., et al., *Tetrahedron Letters*, 35(12), 1833–1834 (1994), C. R. Johnson and S. J. Bis, *Tetrahedron Letters*, 33(48), 7287–7290 (1992), Theil, et al., *Liebieqs Ann. Chem.*, 195–200 (1991), Theil, et al., *Tetrahedron*, 47(36), 7569–7582 (1991) and Theil, et al., *Synthesis*, 540 (1988), to provide the compounds of formula (VIb) and (VII).

For example, a compound of formula (VI) is dissolved in a suitable solvent or solvent mixture, such as tert-butyl methyl ether, diethyl ether, diisopropyl ether, tetrahydrofuran, cyclohexane, toluene, hexane and the like. The preferred suitable solvents are tert-butyl methyl ether and cyclohexane. The solution is treated with a suitable enzyme and an excess of a suitable acylating agent. Examples of suitable acylating agents are isopropenyl acetate, isopropenyl propionate, isopropenyl butyrate, vinyl acetate, vinyl propionate, vinyl butyrate and the like. The preferred suitable acylating agent is vinyl acetate. About 0.70 equivalents of an alkyl amine, such as triethylamine, may be optionally added, with stirring, at a temperature of about 15° C. to about 55° C. The preferred temperature is about 22° C. A suitable enzyme is an enzyme that catalyzes the enantioselective acylation of the compound of formula (VI) whereby essentially only a single enantiomer of the racemic mixture, such as the compound of formula (VIa), is acylated under the described conditions to produce a mixture of compounds of formula (VII) and of formula (VIb), wherein Z is acetyl, propionyl or butyryl. Examples of suitable enzymes are pancreatin (available from Sigma Chemical Company), Candida antarctica lipase B (Novo Nordisk SP 435), lipozyme IM (available from Novo Nordisk) and the like. The preferred suitable enzyme is pancreatin. The reaction is then stirred for about 6 hours to about 30 hours, preferably about 8 hours. The reaction is then filtered through diatomaceous earth and the filtrate is concentrated under vacuum to provide a mixture of compounds of formula (VIb) and (VII). The resulting mixture of compounds of formula (VIb) and (VII) are readily separated from one another by techniques and procedures well known to one of ordinary skill in the art, such as chromatography or distillation. For example, the mixture can be chromatographed on silica gel with a suitable eluent, such as ethyl acetate/hexane to provide a clean separation of compounds of formula (VIb) from compounds of formula (VII).

In Scheme III, step B, the compounds of formula (VII) can be selectively hydrolyzed by procedures well known to one of ordinary skill in the art to produce the compounds of formula (VIa). For example, the compound of formula (VII) wherein Pg is a tetrahydro-pyran-2-yl protecting group, or a trialkylsilyl protecting group, such as a tert-butyldimethylsilyl group, can be dissolved in a suitable solvent or solvent mixture, such as THF/methanol/water, and treated with one equivalent of a suitable base, such as lithium hydroxide monohydrate. The reaction is stirred at room temperature for about 1 to 8 hours and the product is then isolated and purified by techniques well known in the art, such as extractive methods and chromatography. For example, the reaction is diluted with a suitable organic solvent, such as diethyl ether, rinsed with water, dried over anhydrous magnesium sulfate, filtered and concentrated under vacuum. The residue is then purified by chromatography on silica gel with a suitable eluent, such as ethyl acetate/hexane, to provide the compound of formula (VIa).

In Scheme III, step C, the compounds of formula (VII) can be selectively hydrolyzed by procedures well known to one of ordinary skill in the art to produce compounds of formula (VIII). For example, the compound of formula (VII) wherein Pg is a tetrahydro-pyran-2-yl protecting group can be dissolved in a suitable organic solvent such as ethanol, and treated with p-toluenesulfonic acid. In addition, the compound wherein Pg is a tert-butyldimethylsilyl group on formula (IV), can be dissolved in a suitable organic solvent, such as tetrahydrofuran, and treated with n-tetrabutylamonium fluoride. Either of the above reaction mixtures is then stirred at room temperature for about 1 to 8 hours and the product is then isolated and purified by techniques well known in the art, such as extractive methods and chromatography. For example, either of the above reaction mixtures is diluted with a suitable organic solvent, such as diethyl ether, rinsed with water, dried over anhydrous magnesium sulfate, filtered and concentrated under vacuum. The residue is then purified by chromatography on silica gel with a suitable eluent, such as ethyl acetate/hexane, to provide the compound of formula (VIII).

The compounds of formulas (VIb) and (VIa) can then be readily converted to the corresponding enantiomers of O-protected 3-hydroxycyclopentanone by procedures known to one of ordinary skill in the art. For example, the compound of formulas (VIa) or (VIb) is dissolved in a suitable organic solvent, such as methylene chloride and treated with a suitable oxidizing agent, such as pyridinium dichromate (PDC), pyridinium chlorochromate (PCC) or Swern conditions to provide the corresponding ketones.

The following examples present typical syntheses as described in Schemes I, II and III. These examples are understood to be illustrative only and are not intended to limit the scope of the present invention in any way.

Gas chromatography retention times reported herein are obtained under the following conditions; a Hewlett Packard 5890 Series II Gas Chromatograph is utilized, with a 30 m×0.32 mm HP-5 cross-linked, 5% PH ME silicone column fitted thereto. The flow rate is set at 30 mL/min with helium as the carrier gas. The injection port temperature is 200° C., the detector temperature is 275° C. and the program used is a gradient wherein the initial temperature is set at 100° C. for 10 minutes and then it is increased at a rate of 10° C./minute to 200° C. where it is held for 5 minutes prior to terminating.

In addition, chiral chromatography is readily utilized by one of ordinary skill in the art to determine the ee of a particular compound. For example, a CDX-β 10 m×0.25 mm id (available from J & W Scientific, Folsom, Calif.) can be utilized under standard conditions, such as a column temperature of 100° C., injector temperature of 200° C. and detector temperature of 220° C. Alternatively, the ee of a particular compound can be determined by preparing the corresponding Mosher's Esters of the compounds from (R)-(+)-α-methoxy-α-(trifluoromethyl)phenylacetic acid or (S)-(−)-α-methoxy-α-(trifluoromethyl)phenylacetic acid utilizing techniques well known to one of ordinary skill in the art, for example see Dale, J. A., Dull, D. L. and Mosher, H. S. *J. Org. Chem.*, 34(9), 2543–2549 (1969). The amounts of each resulting diastereomer can be determined by $^{19}$F NMR or separation by column chromatography, chiral column chromatography or gas chromatography, as is well known in the art, thereby allowing calculation of the ee of the compound.

As used herein, the following terms have the indicated meanings: "g" refers to grams; "mmol" refers to millimoles; "ml" refers to milliliters; "bp" refers to boiling point; "mp" refers to melting point; "° C." refers to degrees Celsius; "mmHg" refers to millimeters of mercury; "μL" refers to microliters; "μg" refers to micrograms; and "μM" refers to micromolar; "Rf" refers to retention factor; "δ" refers to parts per million downfield from tetramethylsilane; "[α]$_D^{20}$" refers to specific rotation of the D line of sodium at 20° C. obtained in a 1 decimeter cell; "c" refers to concentration in g/mL; "DMF" means dimethylformamide; "THF" means tetrahydrofuran; "TBME" means tert-butyl methyl ether; "NMM" means N-methylmorpholine; "DMSO" means dimethylsulfoxide; and "DMAP" means 4-dimethylaminopyridine.

EXAMPLE 1

Preparation of 4-hydroxy-2-cyclopentenone.

Scheme I, step a; A solution of furfuryl alcohol (125 g, 1.27 mol) in water (3.7L) is treated with KH$_2$PO$_4$ (6.3 g, 46.3 mmol). The pH of the solution is adjusted to pH 4.1 (pH meter) with H$_3$PO$_4$ and then heated to 99° C. under an atmosphere of nitrogen for 40 hours. The solution is then cooled and washed with methylene chloride (2×500 mL). The organic layers are combined and extracted with water (2×500 mL). The aqueous layer and aqueous extracts are combined and concentrated under vacuum (70° C., 20 mm Hg) to provide an oil. The oil is dissolved in methylene chloride (1L), dried over anhydrous magnesium sulfate, filtered and concentrated under vacuum to provide the title compound (66 g, 53%) as a dark oil; $^1$H NMR (CDCl$_3$) δ7.61 (dd, J=5.6, 4.8 Hz, 1H), 6.20 (dd, J=5.6, 4.8 Hz, 1H), 5.01–5.04 (m, 1H), 3.61 (bs, 1H), 2.75 (dd, J=18.5, 3.2 Hz, 1H), 2.26 (dd, J=18.5, 6.0 Hz, 1H); $^{13}$C NMR (CDCl$_3$) δ207.4, 164.0, 134.7, 70.1, 44.1; IR (neat) v$_{max}$ 3387, 2974, 1711 cm$^{-1}$; MS (EI) m/e (% relative intensity) 98 (M$^+$, 100).

Anal. Calcd for C$_5$H$_6$O$_2$ · 0.16H$_2$C, 59.47; H, 6.30, H$_2$0, 2.9.

Found: C, 59.56; H, 6.52, H$_2$O, 3.0.

EXAMPLE 2

Preparation of 4-tert-butyldimethylsiloxy-2-cyclopentenone.

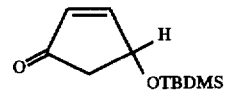

Scheme I, step b; A solution of 4-hydroxy-2-cyclopentenone (191 g, 1.95 mol, prepared in example 1) and triethylamine (430 mL, 3.09 mol) in anhydrous tetrahydrofuran (1L) is treated with 4-dimethylaminopyridine (4.90 g, 40.0 mmol). The solution is cooled to 0° C. and treated portionwise, over 10 minutes, with tert-butyldimethylsilyl chloride (278 g, 1.84 mol) maintaining the temperature at or below 10° C. The reaction is then allowed to stir overnight at room temperature. It is then poured into aqueous HCl (0.5N, 1L). The phases are separated and the aqueous phase is extracted with heptane (2×1L). The organic phase and organic extracts are combined, washed with aqueous HCl (0.5N, 2×500 mL), then 5% sodium bicarbonate (500 mL), then brine (500 mL), dried over anhydrous magnesium sulfate, filtered and concentrated under vacuum (40° C., 20 mmHg) to provide the title compound (325 g). This is purified by Kugelrohr distillation (70°–80° C., 1 mmHg) to provide the title compound (282 g, 72% yield) as a light yellow oil, R$_f$=0.55, 20% ethyl acetate/hexane, GC retention time is 14.97 minutes; $^1$H NMR (CDCl$_3$) δ7.48 (dd, J=5.7, 2.4 Hz, 1H), 6.20 (d, J=5.7 Hz, 1H), 4.95–4.99 (m, 1H), 2.72 (dd, J=18.2, 6.0 Hz, 1H), 2.25 (dd, J=18.2, 2.3 Hz, 1H), 0.88 (s, 9H), 0.11 (s, 6H); $^{13}$C NMR (CDCl$_3$) δ 206.4, 163.8, 134.4, 70.8, 44.9, 25.7, 25.6, 18.0; IR (neat) vmax 2957, 2931, 2887, 2858, 1725 cm$^{-1}$; MS (EI) m/e (% relative intensity) 212 (M$^+$, 5), 155 (M$^+$-57,100).

Anal. Calcd for C$_{11}$H$_{20}$O$_2$Si: C, 62.21; H, 9.51.

Found: C, 62.39; H, 9.50.

EXAMPLE 3a

Preparation of cis-4-tert-butyldimethylsilyloxy-2-cyclopentenol.

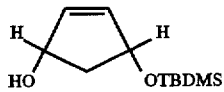

Scheme I, step c; A mechanically stirred solution of 4-tert-butyldimethylsiloxy-2-cyclopentenone (50.2 g, 236 mmol) in anhydrous toluene (1L) under an atmosphere of argon is treated with lithium iodide (160 g, 1.20 mol). The mixture is cooled to −20° C. and treated with lithium aluminum hydride (9.0 g, 237 mmol) in one portion. The reaction is then stirred for 5 minutes and anhydrous tert-butyl methyl ether (200 mL) is added at a rate that maintains the temperature of the reaction at or below −15° C. (total addition time is approximately 3 minutes). The reaction is stirred for one hour at −20° C. and then it is quenched by slow addition of aqueous sodium hydroxide (1N, 250 mL) at a rate that maintains the temperature of the reaction below 20° C. The resulting suspension is then filtered through a pad of diatomaceous earth and the pad is subsequently rinsed with toluene (400 mL). The filtrate phases are separated and the aqueous phase is extracted with toluene (300 mL). The organic phase and organic extract are combined, rinsed with aqueous sodium hydroxide (1N, 300 mL), brine (300 mL), dried over anhydrous magnesium sulfate, filtered and concentrated under vacuum (40° C., 20 mmHg). The residue is then purified by Kugelrohr distillation (60°–80° C., 1 mmHg) to provide the title compound (37.4 g, 74% yield) as a colorless oil; cis/trans/1−2+1−4 addition, 95.3/2.1/2.6; $R_f$=0.20, 20% ethyl acetate/hexane, GC retention time for the title compound is 13.95 minutes, while GC retention times for the byproducts corresponding to compounds 3 (trans) and 4 (1−2+1−4 addition) in Scheme I wherein Pg is a TBDMS group are 14.45 min. and 14.06 min. respectively; for the title compound, $^1$H NMR (CDCl$_3$)δ 5.93 (dt, J=5.5, 1.7 Hz, 1H), 5.84 (dr, J=5.5, 1.6 Hz, 1H), 4.63–4.68 (m, 1H), 4.52–4.62 (m, 1H), 2.76–2.86 (bs, 1H), 2.69 (dr, J=13.8, 7.1 Hz, 1H), 1.52 (dt, J=13.8, 4.7 Hz, 1H), 0.90 (s, 9H), 0.09 (s, 6H); $^{13}$C NMR (CDCl$_3$) δ 136.7, 135.6, 75.1, 75.0, 44.5, 25.9, 18.1; IR (neat) $v_{max}$ 3373, 2957, 2932 cm$^{-1}$; MS (EI) m/e (% relative intensity) 157 (M$^+$-57).

EXAMPLE 3b

Preparation of cis-4-tert-butyldimethylsilyloxy-2-cyclopentenol.

Scheme I, step c; A mechanically stirred solution of 4-tert-butyldimethylsiloxy-2-cyclopentenone (175 g, 824 mmol) in anhydrous toluene (1.5L) under an atmosphere of argon is treated with lithium iodide (240 g, 1.79 mol). The mixture is cooled to −20° C. and treated with lithium aluminum hydride (13.5 g, 356 mmol) in one portion. The reaction is then stirred for 5 minutes and anhydrous tert-butyl methyl ether (300 mL) is added at a rate that maintains the temperature of the reaction at or below −15° C. (total addition time is approximately 3 minutes). The reaction is stirred for 3 hours at −20° C. and then it is quenched by slow addition of aqueous sodium hydroxide (1N, 250 mL) at a rate that maintains the temperature of the reaction below 20° C. The resulting suspension is then filtered through a pad of diatomaceous earth and the pad is subsequently rinsed with toluene (400 mL). The filtrate phases are separated and the aqueous phase is extracted with toluene (450 mL). The organic phase and organic extract are combined, rinsed with aqueous sodium hydroxide (1N, 450 mL), brine (450 mL), dried over anhydrous magnesium sulfate, filtered and concentrated under vacuum (40° C., 20 mmHg). The residue is then purified by Kugelrohr distillation (60°–80° C., 1 mmHg) to provide the title compound (120 g, 68% yield) as a colorless oil; cis/trans/1−2 +1−4 addition, 92/4/4.

EXAMPLE 3c

Preparation of cis-4-tert-butyldimethylsilyloxy-2-cyclopentenol.

Scheme I, step c; A mechanically stirred solution of 4-tert-butyldimethylsiloxy-2-cyclopentenone (1.01 g, 4.76 mmol) in anhydrous ethyl ether (20 mL) under an atmosphere of argon is treated with lithium iodide (3.20 g, 23.9 mmol). The mixture is cooled to −78° C. and treated with lithium aluminum hydride (184 mg, 4.85 mmol) in one portion. The reaction is then stirred for 90 minutes. It is then quenched by slow addition of aqueous sodium hydroxide (1N, 23 mL) at a rate that maintains the temperature of the reaction below 20° C. The resulting suspension is then filtered through a pad of diatomaceous earth and the pad is subsequently rinsed with ether. The filtrate phases are separated and the aqueous phase is extracted with ether (20 mL). The organic phase and organic extract are combined, rinsed with aqueous sodium hydroxide (1N, 20 mL), brine (20 mL), dried over anhydrous magnesium sulfate, filtered and concentrated under vacuum (40° C., 20 mmHg). The residue is then purified by Kugelrohr distillation (60°–80° C., 1 mmHg) to provide the title compound. (820 mg, 80% yield) as a colorless oil; cis/trans/1−2+1−4 addition, 88.5/3.3/8.2.

EXAMPLE 3d

Preparation of cis-4-tert-butyldimethylsilyloxy-2-cyclopentenol.

Scheme I, step c; A mechanically stirred solution of 4-tert-butyldimethylsiloxy-2-cyclopentenone (501 mg, 2.36 mmol) in anhydrous toluene (10 mL) under an atmosphere of argon is treated with lithium bromide (1.06 g, 12.2 mmol). The mixture is cooled to −20° C. with an ice/salt bath and treated with lithium aluminum hydride (92.0 mg, 2.42 mmol) in one portion followed by tert-butyl methyl ether (1.0 mL). The ice/salt bath is replaced with an ice bath and the reaction is then stirred for 2 hours at 0° C. It is then quenched by slow addition of aqueous sodium hydroxide (1N, 7.0 mL) at a rate that maintains the temperature of the reaction below 20° C. The resulting suspension is then filtered through a pad of diatomaceous earth and the pad is subsequently rinsed with toluene. The filtrate phases are separated and the aqueous phase is extracted with toluene. The organic phase and organic extract are combined, rinsed with aqueous sodium hydroxide (1N), brine, dried over anhydrous magnesium sulfate, filtered and concentrated under vacuum (40° C., 20 mmHg). The residue is then purified by Kugelrohr distillation (60°–80° C., 1 mmHg) to provide the title compound (350 mg, 69% yield) as a colorless oil; cis/trans/1−2+1−4 addition, 92.7/6.3/1.0.

EXAMPLE 3e

Preparation of cis-4-tert-butyldimethylsilyloxy-2-cyclopentenol.

Scheme I, step c; A stirred solution of ZnCl$_2$ (19 mL, 19 mmol, 1M in ether) is treated with 4-tert-butyldimethylsiloxy-2-cyclopentenone (2.0 g, 9.42 mmol) under an atmosphere of argon. The solution is cooled to −20°

19

C. and treated dropwise with lithium aluminum hydride (9.0 mL, 9.0 mmol, 1M in ether) at such a rate as to keep the reaction temperature at or below −15° C. After stirring for about 2 hours at −20° C., approximately 5 mL of 1N NaOH was added. The reaction is filtered through diatomaceous earth, dried over anhydrous magnesium sulfate, filtered and concentrated under vacuum to provide the title compound (1.3 g); cis/trans/1−2+1−4 addition 81/3/16.

EXAMPLE 3f

Preparation of cis-4-tert-butyldimethylsilyloxy-2-cyclopentenol.

Scheme I, step c; A stirred solution of 4-tert-butyldimethylsiloxy-2-cyclopentenone (2.0 g, 9.42 mmol) in anhydrous toluene (15 mL) under an atmosphere of argon is treated with $MgBr_2$ (3.5 g, 19.0 mol). The mixture is cooled to −25° C. and treated with lithium aluminum hydride (178 mg, 4.69 mmol) in one portion, followed by addition of anhydrous tert-butyl methyl ether (3.0 mL). The reaction is stirred at −20° C. for 2 hours and then overnight at room temperature. Additional lithium aluminum hydride (178 mg, 4.69 mmol) is added at room temperature and the reaction is stirred for 2 hours. The reaction is then quenched by slow addition of 1N NaOH (5 mL) followed by filtration through diatomaceous earth. The filtrate is dried over anhydrous magnesium sulfate, filtered and concentrated under vacuum to provide the title compound (1.3 g); cis/trans/1−2+1−4 addition, 90/3/7.

EXAMPLE 3g

Preparation of cis-4-tert-butyldimethylsilyloxy-2-cyclopentenol with 2.8 mol % tert-butyldimethylsilanol added to the reaction mixture.

Scheme I, step c; Into a 100 mL flask equipped with a mechanical stirrer, a low temperature thermometer and a 60 mL addition funnel topped with a nitrogen bubbler is placed lithium aluminum hydride (0.5 g, 0.013 mol), lithium iodide (6.7 g, 0.05 mol) and toluene (34 g). The slurry is cooled to −40° C. and the addition funnel is charged with 4-tert-butyldimethylsiloxy-3-cyclopentanone (5.0 g, 0.024 mol, containing 2.8% tert-butyldimethylsilanol as determined by gas chromatography on a Hewlett-Packard 5890 Series II gas chromatograph, a Hewlett-Packard integrator, a Hewlett-Packard column, PH-1, 10 m, 0.53 mm ID, 2.56 μm, injection port at 190° C., detector at 270° C., using a gradient with a starting temperature of 50° C. for 2 minutes then increasing at a rate of 20° C./minute to 250° C. for 5 minutes) and tert-butylmethyl ether (18 g, TBME). The cyclopentenone/TBME solution is added to the slurry over 5 minutes at such a rate as to maintain the internal reaction temperature between −30° C. and −36° C. The reaction mixture is then allowed to warm to −30° C. and stir for 4 hours. The reaction is quenched by slow addition of a 5 wt % solution of aqueous ammonium chloride (20 g). Toluene (20 g) is added and the phases are separated. The aqueous phase is then extracted with toluene (30 g). The organic phases are combined, washed with water (30 g), dried over anhydrous magnesium sulfate, filtered and concentrated under vacuum. The residue is purified by vacuum distillation through a 14 cm, packed glass bead (4 mm) column at 0.2 mmHg (63°–66° C.) to provide the title compound (3.9 g, 77%); cis/trans/1−2+1−4 addition, 95/4/1.

20

EXAMPLE 3h

Preparation of cis-4-tert-butyldimethylsilyloxy-2-cyclopentenol with 16 mol % tert-butyldimethylsilanol added to the reaction mixture.

Scheme I, step c; Into a 100 mL flask equipped with a mechanical stirrer, a low temperature thermometer and a 60 mL addition funnel topped with a nitrogen bubbler is placed lithium aluminum hydride (0.5 g, 0.013 mol), lithium iodide (6.7 g, 0.05 mol) and toluene (34 g). The slurry is cooled to −30° C. and the addition funnel is charged with 4-tert-butyldimethylsiloxy-3-cyclopentanone (4.3 g, 0.02 mol, containing 2.8% tert-butyldimethylsilanol as determined in example 3g), tert-butyldimethylsilanol (0.6 g, 0.005 mol) and tert-butylmethyl ether (18 g, TBME). The additional tert-butyldimethylsilanol is added to adjust the solution to contain 16% tert-butyldimethylsilanol. The cyclopentenone/silanol/TBME solution is added in one portion resulting in an 8° C. exotherm. The reaction mixture is cooled and maintained at between −28° C. and −32° C. for 1.5 hours. The reaction is then quenched by slow addition of a 5 wt % solution of aqueous ammonium chloride (20 g) and the phases are separated. The aqueous phase is extracted with methylene chloride (2×20 g). The organic phases are combined, washed with water (20 g), dried over anhydrous magnesium sulfate, filtered and concentrated under vacuum. The residue is purified by vacuum distillation through a 14 cm packed glass bead (4 mm) column at 0.5 mmHg (67°–70° C.) to provide the title compound (3.5 g, 81%); cis/trans/1−2+1−4 addition, 96.3/2.8/0.9.

EXAMPLE 3I

Preparation of cis-4-tert-butyldimethylsilyloxy-2-cyclopentenol with 17 mol % tert-butyldimethylsilanol added to the reaction mixture.

Scheme I, step c; Into a 100 mL flask equipped with a mechanical stirrer, a low temperature thermometer and a 60 mL addition funnel topped with a nitrogen bubbler is placed lithium aluminum hydride (0.5 g, 0.013 mol), lithium iodide (1.4 g, 0.010 mol) and toluene (34 g). The slurry is cooled to −33° C. and the addition funnel is charged with 4-tert-butyldimethylsiloxy-3-cyclopentanone (4.3 g, 0.02 mol, containing 2.8% tert-butyldimethylsilanol as determined in example 3g), tert-butyldimethylsilanol (0.6 g, 0.005 mol) and tert-butylmethyl ether (18 g, TBME). The additional tert-butyldimethylsilanol is added to adjust the solution to contain 17% tert-butyldimethylsilanol. The cyclopentenone/silanol/TBME solution is added in one portion resulting in an internal temperature of −23° C. The reaction mixture temperature is maintained near −30° C. for 23 hours and it is then quenched with 5 wt % aqueous ammonium chloride (21 g). The phases are separated and the aqueous phase is extracted with toluene (2×20 g). The organic phases are combined, washed with water (25 g), dried over anhydrous magnesium sulfate, filtered and concentrated under vacuum. The residue is purified by vacuum distillation through a 14 cm packed glass bead (4 mm) column at 0.4 mmHg (65°–68° C.) to provide the title compound (3.2 g, 74%); cis/trans/1−2+1−4 addition, 96.2/2.8/1.

EXAMPLE 3J

Preparation of cis-4-tert-butyldimethylsilyloxy-2-cyclopentenol with 18 mol % tert-butyldimethylsilanol added to the reaction mixture.

Scheme I, step c; Into a 100 mL flask equipped with a mechanical stirrer, a low temperature thermometer and a 60 mL addition funnel topped with a nitrogen bubbler is placed lithium aluminum hydride (0.5 g, 0.013 mol) and toluene (30 g). The slurry is cooled to −30° C. and the addition funnel is charged with tert-butyldimethylsilanol (0.6 g, 0.005 mol) and toluene (9 g). The silanol/toluene solution is added in one portion resulting in mild gas evolution. The additional tert-butyldimethylsilanol is added to adjust the solution to contain 18% tert-butyldimethylsilanol. The mixture is stirred at a temperature of between −25° C. and −30° C. for 15 minutes. The addition funnel is charged with 4-tert-butyldimethylsiloxy-3-cyclopentanone (4.3 g, 0.02 mol, containing 2.8% tert-butyldimethylsilanol as determined in example 3g) and tert-butyl methyl ether (13 g, TBME). The cyclopentenone/TBME solution is added in one portion to the slurry resulting in a 9° C. exotherm (−21° C. internal reaction temperature). The reaction mixture temperature is maintained near −25° C. for 1.5 hours and then the reaction is quenched with 5 wt % aqueous ammonium chloride. Toluene (20 g) is added and the phases are separated. The aqueous phase is extracted with toluene (30 g). The organic phases are combined, washed with water (30 g), dried over anhydrous magnesium sulfate, filtered and concentrated under vacuum. The residue is purified by vacuum distillation through a 14 cm packed glass bead (4 mm) column at 0.5 mmHg (67°–69° C.) to provide the title compound (3.1 g, 72%); cis/trans/1–2+1–4 addition, 95/3.9/1.1.

EXAMPLE 3K

Preparation of cis-4-tert-butyldimethylsilyloxy-2-cyclopentenol with 20 mol % isopropanol added to the reaction mixture.

Scheme I, step c; A slurry of lithium aluminum hydride (350 mg, 9 mmol) and lithium iodide (1.16 g, 8.7 mmol) in toluene (34 mL) is cooled to −30° C. and treated with a solution of 4-tert-butyldimethylsiloxy-3-cyclopentanone (3.509 g, 16.5 mmol), tert-butyl methyl ether (17 mL) and isopropanol (0.25 mL, 20 mol %) dropwise over 22 minutes. The temperature rises to −25° C. The reaction is then stirred for 2.5 hours at −20° C. to −25° C. Then saturated ammonium chloride (20 mL) is added to the reaction followed by water (5 mL). The reaction is warmed to room temperature and then filtered. The solids are rinsed with toluene (20 mL). The phases of the filtrate are separated. The aqueous phase is extracted with toluene (20 mL). The organic phases are combined, dried over anhydrous magnesium sulfate, filtered and concentrated under vacuum. The residue is purified by Kugelrohr distillation (0.4 mmHg/ 60°–75° C.) to provide a colorless oil (2.17 g, 61%); cis/trans/1–2+1–4 addition, 95.9/3.1/1.

EXAMPLE 4

Preparation of cis-2-cyclopentenyl-1,4-diol.

Scheme I, step d; A solution of cis-4-tert-butyldimethylsilyloxy-2-cyclopentenol (50 g, 0.233 mol) in tetrahydrofuran (250 mL) at room temperature is treated sequentially with triethylamine (5.00 mL, 0.036 mol) and tetrabutylammonium fluoride (250 mL of a 1.0 N solution in tetrahydrofuran, 0.250 mol). The reaction is stirred for 3 hours and then concentrated under vacuum (40° C., 20 mmHg). The residue is then purified by chromatography (silica gel, 100×160 mm, 10% acetone/ethyl acetate) followed by recrystallization from chloroform to provide the title compound (18.0 g, 77%) as white needles; mp 57°–58° C., $R_f$=0.25 (10% acetone/ethyl acetate); $^1$H NMR (CDCl$_3$) δ 6.01 (s, 2H), 4.62–4.68 (m, 1H), 4.02 (d, J=7.3 Hz, 1H), 2.73 (dt, J=14.6, 7.3 Hz, 1H), 1.57 (dt, J=14.5, 3.4 Hz, 1H); $^{13}$C NMR (CDCl$_3$) δ136.3, 74.9, 43.3; IR (KBr) $v_{max}$ 3402, 3391, 3364 cm$^{-1}$; MS (CI) m/e (% relative intensity) 83 (M$^+$+H-H$_2$O, 100).

Anal. Calcd for C$_5$H$_8$O$_2$: C, 59.98; H, 8.05.

Found: C, 59.79; H, 8.36.

EXAMPLE 5

Preparation of 4-(tetrahydro-pyran-2-yloxy)-cyclopent-2-enone.

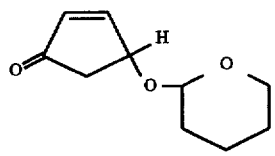

Scheme I, step b; A solution of 4-hydroxy-2-cyclopentenone (1.41 g, 14.4 mmol) in tetrahydrofuran (24 mL) is treated with 3,4-dihydro-2H-pyran (2 mL) and pyridinium p-toluenesulfonate (500 mg, PPTS). The reaction is stirred at room temperature for 18 hours. The reaction mixture is then diluted with ethyl acetate (25 mL) and washed with 50% saturated brine (2×30 mL). The organic layer is dried over anhydrous magnesium sulfate, filtered and concentrated under vacuum. The resulting crude brown oil is purified by filtration through a plug of silica gel (25 g, 33% ethyl acetate/hexane) to provide the title compound as a yellow oil (2.00 g, 76%); $^1$H NMR (CDCl$_3$) δ7.46 (2×dd, 1H, J=16.3, 5.7 Hz), 6.2 (m, 1H), 4.9 (m, 1H), 4.80 (d appt, 1H, J=23.8, 2.9 Hz), 3.9 (m, 1H), 3.6 (m, 1H), 2.73 (2×dd, 1H, J=18.4, 6.2 Hz), 2.35 (2×d, 1H, J=18.4 Hz), 1.8 (m, 1H), 1.6 (m, 4H); IR (neat) $v_{max}$ 2944, 2870, 2855, 1723, 1348, 1202, 1182, 1152, 1128, 1078, 1032 cm$^{-1}$; MS (CI) m/e (% relative intensity) 183 (M+H$^+$, 28), 85(100).

EXAMPLE 6

Preparation of cis-4-(tetrahydro-pyran-2-yloxy)-cyclopent-2-enol.

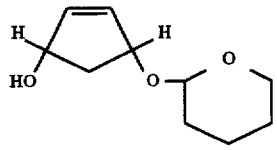

Scheme I, step c; A slurry of lithium aluminum hydride (222 mg, 5.8 mmol), lithium iodide (3.2 g, 24 mmol), tert-butyl methyl ether (6 mL) and toluene (16 mL) is cooled to −15° C. A solution of 4-(tetrahydro-pyran-2-yloxy)-cyclopent-2-enone (2.179 g, 11.97 mmol, prepared in example 5) in tert-butyl methyl ether (2 mL) and toluene (2 mL) is added dropwise over 40 minutes. The reaction mixture is allowed to stir for 30 minutes. Then sodium hydroxide (1N, 5 mL) is added slowly to the reaction mixture. The slurry is filtered and the resulting phases separated. The aqueous phase is extracted with ethyl acetate (2×10 mL). The organic extracts are combined with the organic phase, dried over magnesium sulfate, filtered and concentrated under vacuum. The crude oil is then purified by chromatography (silica gel, 30 g, 50% ethyl acetate/hexane, 400 mL) to provide the title compound (1.62 g, 73%), cis/trans/1–2+1–4 addition, 88/8/4; $^1$H NMR (CDCl$_3$) δ6.1 (m, 1H), 4.7 (m, 1H), 4.6 (m, 2H), 3.9 (m, 1H), 3.5 (m, 1H), 2.7 (m, 1H), 1.4–2.0 (m, 8H); $^{13}$C NMR (CDCl$_3$) δ 137.2, 137.1, 134.8, 133.6, 98.3, 97.8, 79.7, 79.5, 74.7, 74.5, 62.6, 62.5, 42.0, 41.1, 31.1, 30.9, 25.4, 19.6, 19.5; IR (neat) ν$_{max}$ 2944, 2870, 2855, 1723, 1348, 1202, 1182, 1152, 1128, 1078, 1032 cm$^{-1}$; MS (CI) m/e (% relative intensity) 183 (M+H$^+$, 7), 167 (M+H$^+$-H$_2$O, 40), 85(100).

EXAMPLE 7

Preparation of cis-2-cyclopentenyl-1,4-diol.

Scheme I, step d; A solution of cis-4-(tetrahydro-pyran-2-yloxy)-cyclopent-2-enol (338 mg, prepared in example 6) in ethanol (4 mL) is treated with p-toluenesulfonic acid monohydrate (38 mg, p-TsOH.H$_2$O). The reaction is stirred at room temperature for 2 hours. Potassium carbonate (116 mg) is added and the reaction mixture is diluted with 25% hexane/ethyl acetate (10 mL). This solution is poured onto a plug of silica gel (10 g) and eluted with 25% hexane/ethyl acetate (3×30 mL) and ethyl acetate (2×40 mL) to provide the title compound (167 mg, 90%), cis/trans/1–2+1–4 addition, 88/8/4.

EXAMPLE 8

Preparation of 4-tert-butoxy-cyclopent-2-enone.

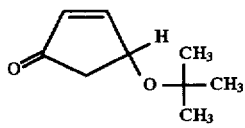

Scheme I, step b; A solution of 4-hydroxy-2-cyclopentenone (1.15 g, 11.7 mmol) in methylene chloride is cooled to 3° C. and treated sequentially with tert-butyl trichloroacetimidate (4.2 mL, 23.7 mmol) and boron trifluoride diethyl etherate (0.15 mL). The reaction mixture is stirred at 3–10° C. for 2 hours and then allowed to warm to room temperature and stirred for 22 hours. The reaction mixture is then treated with sodium bicarbonate (250 mg) and filtered. The filtrate is concentrated under vacuum and the residue is purified by chromatography (silica gel, 39 g, 20% ethyl acetate/hexane, 600 mL) to provide the title compound (355 mg, 40%) as a yellow oil; $^1$H NMR (CDCl$_3$) δ7.44 (dd, 1H, J=18 Hz), 6.2 (d, 1H, J=5.4 Hz), 4.8 (m, 1H), 2.68 (dd, 1H, J=5.8, 18 Hz), 2.25 (d, 1H, J=18 Hz), 1.27 (s, 9H); IR (neat) ν$_{max}$ 2976, 2936, 1721, 1368, 1352, 1188, 1103, 1161 cm$^{-1}$; MS (CI) m/e (% relative intensity) 155 (M+H$^+$, 22), 99 (100).

EXAMPLE 9

Preparation of cis-4-tert-butyloxy-cyclopent-2-enol.

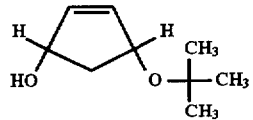

Scheme I, step C; A slurry of lithium aluminum hydride (55 mg, 1.44 mmol), lithium iodide (1.65 g, 5.76 mmol), tert-butyl methyl ether (2 mL) and toluene (3 mL) is cooled to −15° C. The slurry is treated dropwise with 4-tert-butoxy-cyclopent-2-enone(430 mg, 2.79 mmol, dissolved in 1 mL of toluene) over 5 minutes. The reaction mixture is stirred at −20° C. to −12° C. for 2 hours and then allowed to warm to room temperature and is stirred for 30 minutes. The reaction mixture is then treated sequentially with sodium hydroxide (1N, 1 mL), then tert-butyl methyl ether (10 mL) and filtered. The phases of the filtrate are separated and the aqueous phase is extracted with tert-butyl methyl ether (15 mL). The organic extracts and organic phase is combined, dried over magnesium sulfate, filtered and concentrated under vacuum. The residue is purified by chromatography (silica gel, 30 g, 33% ethyl acetate/hexane) to provide the title compound (183 mg, 42%) as a yellow oil, cis/trans/1–2+1–4 addition, 87/9.8/3.2; $^1$H NMR (CDCl$_3$) 6 5.9 (m, 1H), 5.8 (m, 1H), 4.6 (m, 1H), 4.5 (m, 1H), 2.7 (m, 1H), 2.0 (d,1H, J=9.6 Hz), 1.5 (d appt, 1H, J=4.5, 14 Hz), 1.2 (s, 9H); $^{13}$C NMR (CDCl$_3$) δ136.6, 36, 75.5, 74.4, 74, 44.6, 28.7; ν$_{max}$ 3395, 2974, 2938, 907, 2878, 1389, 1364, 1117, 1169, 1022 cm$^{-1}$; MS (CI) m/e (% relative intensity) 157 (M+H$^+$ -H$_2$O), 57, 83 (100).

EXAMPLE 10

Preparation of (−)-cis-4-tert-butyldimethylsilyloxy-2-cyclopentenol (A) and (−)-acetic acid 4-tert-butyldimethylsilyloxy-cyclopent-2-enyl ester (B).

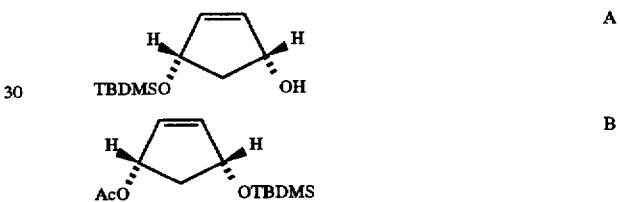

Scheme II, step A; Cis-4-tert-butyldimethylsilyloxy-2-cyclopentenol (10.0 g, 46.6 mmol, prepared in example 3a) is dissolved in tert-butyl methyl ether (60 mL, anhydrous). To the solution is added triethylamine (4.5 mL, 32.3 mmol), pancreatin (30 g, available from Sigma Chemical Company), and vinyl acetate (22 mL, 239 mmol). The reaction is allowed to stir for 7 hours at room temperature. The reaction is then filtered through diatomaceous earth and the filtrate is concentrated under vacuum. The products are separated by chromatography on silica gel (5% to 20% ethyl acetate/hexane) to provide (−)-acetic acid 4-tert-butyldimethylsilyloxy-cyclopent-2-enyl ester (B, 6.1 g, 51% yield, 99% ee), [α]$_D$ −0.2°, (c=0.52, chloroform) as a yellow oil and (−)-cis-4-tert-butyldimethylsilyloxy-2-cyclopentenol (A, 4.7 g, 47% yield, >99% ee), [α]$_D$ −18.6°, (c=1.01, chloroform) as a yellow oil.

EXAMPLE 11

Preparation of (−)-cis-4-(tetrahydro-pyran-2-yloxy)-cyclopent-2-enol (A) and (−)-acetic acid cis-4-(tetrahydro-pyran-2-yloxy)-cyclopent-2-enyl ester (B).

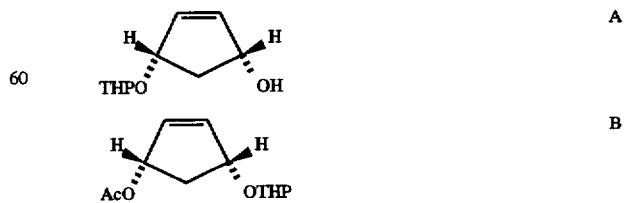

Scheme II, step A; Cis-4-(tetrahydro-pyran-2-yloxy)-cyclopent-2-enol (1.091 g, 5.92 mmol, prepared in example 6) is dissolved in tert-butyl methyl ether (8.6 mL, anhydrous). To the solution is added triethylamine (0.59 mL, 4.2 mmol), pancreatin (3.2 g, available from Sigma Chemical Company), and vinyl acetate (2.7 mL, 29 mmol). The reaction is allowed to stir for 7 hours at room temperature. The reaction is then filtered through diatomaceous earth and the filtrate is concentrated under vacuum. The products are separated by chromatography on silica gel (10% to 20% ethyl acetate/hexane) to provide (–)-acetic acid cis-4-(tetrahydro-pyran-2-yloxy)-cyclopent-2-enyl ester (B, 601 mg, 45% yield, 91% ee) $[\alpha]_D$=–19.8°,(c=1.00, chloroform) as a yellow oil and (–)-cis-4-(tetrahydro-pyran-2-yloxy)-cyclopent-2-enol (A, 560 mg, 50% yield, 94% ee), $[\alpha]_D$=–9.9°, (c=1.06, chloroform) as a yellow oil.

(–)-cis-4-(tetrahydro-pyran-2-yloxy)-cyclopent-2-enol

Anal. Calcd for $C_{11}H_{16}O_3 \cdot 0.13H_2O$:C, 64.38; H, 8.78.
Found: C, 64.32; H, 8.97.

(–)-acetic acid cis-4-(tetrahydro-pyran-2-yloxy)-cyclopent-2-enyl ester

Anal. Calcd for $C_{12}H_{18}O_4$: C, 63.70; H, 8.01.
Found: C, 63.42; H, 8.09.

EXAMPLE 12

Preparation of (+)-cis-4-tert-butyldimethylsilyloxy-2-cyclopentenol.

Scheme II, step B; Dissolve (–)-acetic acid 4-tert-butyldimethylsilyloxy-cyclopent-2-enyl ester (2.3 mmol, prepared in example 10) in THF/methanol/water (2.7/0.9/0.9 mL). Add lithium hydroxide monohydrate (2.5 mmol) with stirring. After stirring for about 3 hours at room temperature, dilute the reaction with water (10 mL) and extract with tert-butyl methyl ether. Combine the organic phases, dry over anhydrous magnesium sulfate, filter and concentrate under vacuum. Purify the residue by flash chromatography (silica gel, 20% ethyl acetate/hexane) to provide the title compound (452 mg, 92% yield) $[\alpha]^{20}_D$=+21.8°, (c=1.02, chloroform).

EXAMPLE 13

Preparation of (+)-cis-4-(tetrahydro-pyran-2-yloxy)-cyclopent-2-enol.

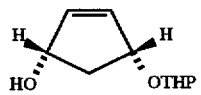

Scheme II, step B; Dissolve (–)-acetic acid cis-4-(tetrahydro-pyran-2-yloxy)-cyclopent-2-enyl ester (106 mg, 0.47 mmol, prepared in example 11) in THF/methanol/water (1.5/0.5/0.5 mL). Add lithium hydroxide monohydrate (0.57 mmol) with stirring. After stirring for about 3 hours at room temperature, dilute the reaction with tert-butyl methyl ether (10 mL) and water (10 mL). Extract with tert-butyl methyl ether (2×10 mL). Combine the organic extracts, dry over anhydrous magnesium sulfate, filter and concentrate under vacuum. Purify the residue by flash chromatography (silica gel, 2.5 g, 1.7×2.5 cm column, 50% ethyl acetate/hexane, 150 mL) to provide the title compound (80 mg, 93% yield), $[\alpha]^{20}_D$=+9.9°, (c=0.98, chloroform).

EXAMPLE 14

Preparation of (–)-cis-4-tert-butyloxy-cyclopent-2-enol (A) and (–)-acetic acid cis-4-tert-butyloxy-cyclopent-2-enyl ester (B).

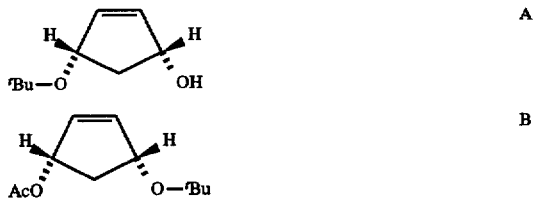

Scheme II, step A; Cis-4-tert-butyloxy-cyclopent-2-enol (485 mg, 3.1 mmol, prepared in example 9) is dissolved in tert-butyl methyl ether (8.6 mL, anhydrous). To the solution is added triethylamine (0.7 eq), pancreatin (3 wt eq, available from Sigma Chemical Company), and vinyl acetate (5 eq). The reaction is allowed to stir for 17 hours at room temperature. The reaction is then filtered through diatomaceous earth and the filtrate is concentrated under vacuum. The products are separated by chromatography on silica gel (10% to 20% ethyl acetate/hexane) to provide (–)-acetic acid cis-4-tert-butyloxy-cyclopent-2-enyl ester (B, 50% yield, 76% ee), $[\alpha]_D$=–10.9°, (c=0.98, chloroform). $^1$H NMR (CDCl$_3$) δ5.94 (d, 1H, J=5.5 Hz), 5.89 (d, 1H, J=5.5 Hz), 5.46 (appt, 1H, J=5.5 Hz), 4.52 (appt, 1H, J=5.5 Hz), 2.8 (m, 1H), 2.0 (s, 3H), 1.6 (d appt, 1H, J=4.8, 14 Hz), 1.22 (s, 9H); $^{13}$C NMR (CDCl$_3$) δ171.2, 138.6, 131.6, 77.4, 77.2, 41, 28.7, 28.6, 21.4; IR (neat) $v_{max}$ 2976, 1738, 1364, 1242, 1196, 1067, 1020 cm$^{-1}$; CIMS m/e (% relative intensity) 199 (M+H$^+$, 4), 139 (M+H$^+$-AcOH, 70), 83 (100), and (–)-cis-4-tert-butyloxy-cyclopent-2-enol (A, 194 mg, 40% yield, >98% ee), $[\alpha]_D$ 17.2°, (c=1.09, chloroform) as a yellow oil.

(–)-cis-4-tert-butyloxy-cyclopent-2-enol

Anal. Calcd for $C_9H_{16}O_2$: C, 69.19; H, 10.32.
Found: C, 69.07; H, 10.37.

(–)-acetic acid cis-4-tert-butyloxy-cyclopent-2-enyl ester

Anal. Calcd for $C_{11}H_{18}O_3$: C, 66.64; H, 9.15.
Found: C, 67.11; H, 9.03.

EXAMPLE 15

Preparation of (+)-cis-4-tert-butyloxy-cyclopent-2-enol.

Scheme II, step B; Dissolve (–)-acetic acid cis-4-tert-butyloxy-cyclopent-2-enyl ester (90 mg, 0.45 mmol, prepared in example 14) in THF/methanol/water (1.5/0.5/0.5 mL). Add lithium hydroxide monohydrate (23.7 mg) with stirring. After stirring for about 2 hours at room temperature, dilute the reaction with water (10 mL) and extract with tert-butyl methyl ether. Combine the organic phases, dry over anhydrous magnesium sulfate, filter and concentrate under vacuum. Purify the residue by flash chromatography (silica gel, 2 g, 40% diethyl ether/hexane, 1.5×2.5 cm column) to provide the title compound (71 mg, quantitative yield, 76% ee) as a pale yellow oil, $[\alpha]^{20}_D$=+14.6°, (c=1.03, chloroform).

EXAMPLE 16

Preparation of cis-4-benzyloxy-cyclopent-2-enol

Scheme I, step b; In a manner analogous to the procedure described in example 8, 4-benzyloxy-2-cyclopent-2-enone is prepared from 4-hydroxy-2-cyclopentenone, benzyl trichloroacetimidate and boron trifluoride diethyl etherate.

Scheme I, step c; A solution of lithium aluminum hydride (45 mg, 1.2 mmol) and lithium iodide (451 mg, 3.37 mmol) in diethyl ether (4 mL) is cooled to −30° C. and treated dropwise over 5 minutes with a solution of 4-benzyloxy-2-cyclopent-2-enone (444 mg, 2.36 mmol, prepared above) in diethyl ether (1 mL). The reaction mixture is stirred for 1.5 hours at −25° C. and then treated with 1N sodium hydroxide (1 mL). The reaction mixture is then allowed to warm to room temperature and is filtered. The filtrate is extracted with ethyl acetate (2×10 mL). The organic phase is dried over anhydrous magnesium sulfate, filtered and concentrated under vacuum. The residue is purified by chromatography to provide the title compound (151 mg, 34% yield) as a pale yellow oil, 28/4/3, cis/trans/1,4 +1,2; $^1$H NMR (CDCl$_3$) δ 7.3 (m, 5H), 6.05 (appt, 2H, J=7 Hz), 4.6 (m, 1H), 4.56 (dd, 2H, J=11.7, 17 Hz), 4.44 (dd, 1H, J=4, 6.8 Hz), 2.7 (m, 1H), 1.67 (d appt, 1H, J=4, 14 Hz); $^{13}$C NMR (CDCl$_3$) δ138.6, 137.4, 134.5, 128.7, 128.1, 127.9, 81.7, 75.3, 71.3, 41.3; IR (neat) $v_{max}$ 3381, 2918, 2851, 1360, 1072, 1051, 1028 cm$^{-1}$; CIMS m/e (% relative intensity) 173 (M+H$^+$—H$_2$O), 91 (100).

Anal. Calcd for C$_{12}$H$_{14}$O$_2$: C, 75.77; H, 7.41.
Found: C, 75.61; H, 7.78.

EXAMPLE 17

Preparation of (−)-cis-4-benzyloxy-cyclopent-2-enol (A) and (−)-acetic acid cis-4-benzyloxy-cyclopent-2-enyl ester (B).

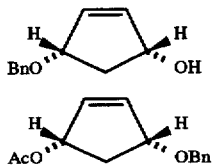

Scheme II, step A; Cis-4-benzyloxy-cyclopent-2-enol (500 mg, prepared in example 16) is dissolved in tert-butyl methyl ether (8.6 mL, anhydrous). To the solution is added triethylamine (0.7 eq), pancreatin (3 wt eq, available from Sigma Chemical Company), and vinyl acetate (5 eq). The reaction is allowed to stir for 7 hours at room temperature. The reaction is then filtered through diatomaceous earth and the filtrate is concentrated under vacuum. The products are separated by chromatography on silica gel (20% ethyl acetate/hexane) to provide (−)-cis-4-benzyloxy-cyclopent-2-enol (A) (147 mg, 29% yield) [α]$^{20}_D$−12°, (c=1.09, chloroform), and (−)-acetic acid cis-4-benzyloxy-cyclopent-2-enyl ester (B) (427 mg, 70% yield),[α]$^{20}_D$=−5.2°,(c=0.97, chloroform). $^1$H NMR (CDCl$_3$) δ 7.3 (m, 5H), 6.13 (d, 1H, J=5 Hz), 5.99 (d, 1H, J=5 Hz), 5.5 (m, 1H), 4.59 (d, 1H, J=11.8 Hz), 4.54 (d, 1H, J=11.8 Hz), 4.5 (m, 1H), 2.78 (d appt, 1H, J=7.2, 14.3 Hz), 2.05 (s, 3H), 1.76 (d appt, 1H, J=4.4, 14.3 Hz); $^{13}$C NMR (CDCl$_3$) δ171.1, 138.5, 136.4, 133.1, 128.7, 128, 127.9, 81.4, 77.1, 71.2, 37.8, 21.4.

EXAMPLE 18

Preparation of (+)-cis-4-benzyloxy-cyclopent-2-enol.

Scheme II, step B; Dissolve (−)-acetic acid cis-4-benzyloxy-cyclopent-2-enyl ester (158 mg, 0.68 mmol, prepared in example 17) in THF/methanol/water (1.5/0.5/0.5 mL). Add lithium hydroxide monohydrate (0.75 mmol) with stirring. After stirring for about 2 hours at room temperature, dilute the reaction with water (10 mL) and extract with tert-butyl methyl ether. Combine the organic phases, dry over anhydrous magnesium sulfate, filter and concentrate under vacuum. Purify the residue by flash chromatography (silica gel, 2 g, 20% ethyl acetate/hexane, 1.5×2.5 cm column) to provide the title compound (120 mg, 92% yield), [α]$^{20}_D$=+5.0°, (C=0.93, chloroform).

EXAMPLE 19

Preparation of (−)-cis-4-acetoxy-cyclopent-2-enol.

Scheme II, step B; Dissolve (−)-acetic acid cis-4-tert-butyldimethylsilyloxy-cyclopent-2-enyl ester (11.53 g, 45 mmol, prepared in example 10) in tetrahydrofuran (49.5 mL) and triethylamine (0.7 mL). Treat the solution with a solution of tetra-n-butylammonium fluoride (49.5 mL of a 1M solution in THF, 49.5 mmol) and stir for 2 hours at room temperature. Then concentrate the reaction under vacuum and purify the residue by chromatography (silica gel, 33% to 50% ethyl acetate/hexane) to provide a white solid (5.85 g) which is recrystallized from tert-butyl methyl ether/heptane (80 mL/100 mL) to provide the title compound (4 99 g, 78% yield, >98% ee), [α]$^{20}_D$ =−68°, (c=0.98, chloroform), mp 48°–49° C.; $^1$H NMR (CDCl$_3$) δ6.12–6.14 (m, 1H), 5.99–6.01 (m, 1H), 5.49–5.54 (m, 1H), 4.70–4.77 (m, 1H), 2.83 (dt, 1H, J=14.5, 7.3 Hz), 2.22 (d, 1H, J=7.8 Hz), 2.08 (s, 3H), 1.6 (dt, 1H, J=14.5, 3.8 Hz).

EXAMPLE 20

Preparation of (+)-acetic acid cis-4-tert-butyldimethylsilyloxy-cyclopent-2-enyl ester.

Dissolve (−)-cis-4-tert-butyldimethylsilyloxy-2-cyclopentenol (1 g, 4.67 mmol, prepared in example 10) in pyridine (20 mL) and treat with acetic anhydride (2 mL). Stir the reaction overnight. Dilute the reaction with diethyl ether (100 mL), wash with 3M hydrochloric acid (3×100 mL), saturated sodium bicarbonate (100 mL), brine (100 mL), dry over anhydrous magnesium sulfate, filter and concentrate under vacuum to provide the title compound (1 g, 98% yield) R$_f$=0.5 (5% ethyl acetate/hexane) [α]$^{20}_D$=+1.3°, (c=1.00, chloroform). $^1$H NMR (CDCl$_3$)δ5.9 (m, 1H), 5.5 (m, 1H), 4.7 (m, 1H), 2.8 (m, 1H), 2.05 (s, 3H), 1.6 (m, 1H), 0.91 (s, 9H), 0.09 (s, 6H); $^{13}$C NMR (CDCl$_3$) δ170.8, 138.8, 131.1, 76.9, 74.8, 41.1, 25.8, 21.1, 18.1, −4.7, −4.6; IR (neat)

$v_{max}$ 2955, 2932, 2859, 1739, 1369, 1240, 1105, 1062, 1049 cm$^{-1}$; CIMS m/e (% relative intensity) 256 (M+H$^+$, 7), 197 (M+H$^+$—AcOH, 100).

Anal. Calcd for C$_{13}$H$_{24}$O$_3$Si: C, 60.90; H, 9.43.

Found: C, 60.89; H, 9.67.

EXAMPLE 21

Preparation of (+)-acetic acid cis-4-(tetrahydro-pyran-2-yloxy)-cyclopent-2-enyl ester (B).

Dissolve (−)-cis-4-(tetrahydro-pyran-2-yloxy)-cyclopent-2-enol (292 mg, 1.59 mmol, prepared in example 11) in pyridine (2.8 mL) and treat with acetic anhydride (0.39 mL) and dimethylaminopyridine (16 mg). Stir the reaction overnight. Concentrate the reaction under vacuum, dissolve the residue with ethyl acetate (10 mL). Wash with 0.5M hydrochloric acid that is ½ saturated with brine (2×10 mL), saturated sodium bicarbonate (10 mL), brine (10 mL), dry over anhydrous magnesium sulfate, filter and concentrate under vacuum. Purify the residue by chromatography (silica gel, 10 g, 1.5×4 cm columnar 20% ethyl acetate/hexane) to provide the title compound (290 mg, 81%).

EXAMPLE 22

Preparation of (−)-cis-4-acetoxy-cyclopent-2-enol.

Dissolve (−)-acetic acid cis-4-(tetrahydro-pyran-2-yloxy)-cyclopent-2-enyl ester (192 mg, 0.85 mmol, prepared in example 11) in ethanol (1.5 mL) and treat with p-toluenesulfonic acid (11.7 mg). Stir the reaction at room temperature for 2 hours. Add carbonate or bicarbonate to neutralize the reaction mixture and concentrate under vacuum. Purify the residue by chromatography (silica gel, 3 g, 1.5×3 cm column, 33% ethyl acetate/hexane, 80 mL), to provide the title compound (90 mg, 75% yield, 91% ee), [α]$^{20}$$_D$=−66.1°, (c=0.63, chloroform).

EXAMPLE 23

Preparation of (−)-cis-3-acetoxy-cyclopentanol.

Dissolve (−)-cis-4-acetoxy-cyclopent-2-enol (11.0 g, 77.4 mmol, prepared in example 19) in ethanol (50 mL) and treat with Raney nickel (1.1 g, previously washed with water (2×50 mL) and ethanol (2×50 mL), Ra—Ni). Charge the atmosphere with hydrogen at 50 psi (344.74 kPa) and shake the mixture. After 20 minutes, filter the solution and treat the filtrate with triethylamine (1.0 mL, 7.2 mmol). After one hour concentrate the solution under vacuum and distill the residue by Kugelrohr distillation (60°–80° C., 1 mm Hg), to provide the title compound (9.74 g, 87%) as a colorless oil.

EXAMPLE 24

Preparation of (1Sr3R)-acetic acid 3-methanesulfonyloxygyclopentyl ester.

Dissolve (1S,3R)-cis-3-acetoxy-cyclopentanol (9.75 g, 67.6 mmol, prepared in example 23) in tert-butyl methyl ether (80 mL, anhydrous) and cool to −8° C. with stirring. Add methanesulfonyl chloride (5.7 mL, 73.6 mmol, mesyl chloride) over 5 minutes, followed by dropwise addition of triethylamine (11.4 mL, 81.2 mL), over about 30 minutes, maintaining the temperature below −2° C. The ice bath is then removed and the mixture is stirred for 2 hours. The mixture is poured into a water/brine mixture (50 mL/50 mL). The layers are separated and the aqueous layer extracted with tert-butyl methyl ether (100 mL). The organic layer and extract is combined, dried over anhydrous magnesium sulfate, filtered and concentrated under vacuum to provide the title compound (14.4 g) as a yellow oil; $^1$H NMR (CDCl$_3$) δ5.1 (m, 2H), 3.02 (s, 3H), 2.41 (m, 1H), 2.05 (s, 3H), 2.0 (m, 5H).

EXAMPLE 25

Preparation of (−)-cis-3-tert-butyldimethylsilyloxycyclopentanol.

Dissolve (−)-cis-4-tert-butyldimethylsilyloxy-2-cyclopentenol (28.85 g, 135 mmol, prepared in example 10) in ethanol (75 mL) and treated with Raney nickel (1.85 g, 32 mmol, previously washed with water (2×50 mL) and ethanol (2×50 mL)). Charge the atmosphere with hydrogen at 50 psi (344.74 kPa) and shake the mixture. After 5.25 hours, filter the reaction. Cool the filtrate to 0° C. and treat with sodium borohydride (0.54 g, 14.3 mmol). After stirring for 2 hours, concentrate the solution under vacuum and distill the resulting oil by Kugelrohr distillation (40°–60° C., 1 mmHg) to provide the title compound (25.5 g, 87%) as a colorless oil, [α]$^{20}$=−3.9°, (c=0.99, chloroform); $^1$H NMR (CDCl$_3$) δ4.4 (m, 1H), 4.3 (m, 1H), 3.03 (d, 1H, J=10.5 Hz), 1.9–1.6 (m, 6H), 0.89 (s, 9H), 0.07 (s, 6H); $^{13}$C NMR (CDCl$_3$) δ74.9, 74.1, 44.4, 34.2, 34.1, 25.8, 17.9, −4.9, −5.0; IR (neat) $v_{max}$ 3405, 2957, 2932, 2888, 2858, 1256, 1091, 1069, 1038, 1026 cm$^{-1}$; CIMS m/e (% relative intensity) 217 (M+H$^+$81), 199 (M+H$^+$—H$_2$O, 37) 67 (100). This (−)-enantiomer (title compound) could not be separated from the (+)-enantiomer (antipode) using the previously described chiral column.

Anal. Calcd for C$_{11}$H$_{24}$O$_2$Si: C, 61.06; H, 11.17.

Found: C, 61.28; H, 10.85.

The above reductions in examples 23 and 25 may also be effected using such catalysts as platinum on Al$_2$O$_3$, nickel boride, platinum on CaCO$_3$, Wilkinson's Catalyst ([C$_6$H$_5$)$_3$P]$_3$RhCl) and the like.

EXAMPLE 26

Preparation of (1S,3R)-methanesulfonic acid 3-tert-butyldimethylsilyloxy-cyclopentyl ester.

Dissolve (−)-cis-3-tert-butyldimethylsilyloxy-cyclopentanol (9.20 g, 42.5 mmol) in anhydrous tert-butyl methyl ether (50 mL) and cool to −5° C. Treat the solution with methanesulfonyl chloride (3.6 g, 46.5 mmol, mesyl chloride), followed by triethylamine (7.2 mL, 51.7 mmol), at such a rate as to keep the temperature between −5° C. and −2° C. with an ice bath. The ice bath is removed and the solution is stirred for 2 hours. The mixture is then transferred to a separatory funnel and treated with brine/water (50 mL/50 mL). The layers are separated and the aqueous layer is extracted with tert-butyl methyl ether (2×50 mL). The organic layer and extracts are combined, washed with brine, dried over anhydrous magnesium sulfate, filtered and concentrated under vacuum to provide the title compound (12.1 g, 97% yield) as a colorless oil; $^1$H NMR (CDCl$_3$) δ5.1 (m, 1H), 4.2 (m, 1H), 2.99 (s, 3H), 2.3 (m, 1H), 2.0 (m, 3H), 1.8 (m, 2H), 0.88 (s, 9H), 0.05 (s, 6H).

EXAMPLE 27

Preparation of 4-trityloxy-2-cyclopentenone.

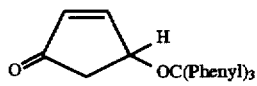

Scheme I, step b; A solution of trityl chloride (3.44 g, 12.3 mmol) in methylene chloride (20 mL) is treated sequentially with 1,8-diazabicyclo[5.4.0]undec-7-ene (2.2 mL, 14.7 mmol, DBU) and 4-hydroxy-2-cyclopentenone (1.01 g, 10.0 mmol, in 5 mL of methylene chloride, prepared in example 1). The reaction is stirred for 3 days at room temperature and then poured onto ice (approximately 25 mL). The phases are separated and the organic phase is washed with water (25 mL). The organic phase is dried over anhydrous magnesium sulfate, filtered and concentrated under vacuum. The residue is purified by column chromatography (silica gel, 10–20% ethyl acetate/hexane) to provide the title compound (1.26 g, 36%) as a pale yellow oil; $^1$H NMR (CDCl$_3$) δ7.5 (m, 6H), 7.3 (m, 9H), 6.85 (dd, 1H), 6.05 (d, 1H), 4.8 (m, 1H), 2.1 (m, 2H); $^{13}$C NMR (CDCl$_3$) δ206.6, 162.9, 144.3, 135.2, 128.8, 128.4, 127.7, 88.2, 73.1, 43.4; IR (KBr) $v_{max}$ 3061, 1719, 1491, 1449, 1352, 1181, 1107, 1053 cm$^{-1}$.

EXAMPLE 28

Preparation of (+/−)-cis-4-trityloxy-2-cyclopentenol.

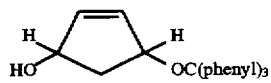

Scheme I, step C; A slurry of 4-trityloxy-2-cyclopentenone (1.03 g, 3.03 mmol, prepared in example 27) in toluene (8 mL) is cooled to −20° C. and treated sequentially with lithium aluminum hydride (76 mg, 2.0 mL), lithium iodide (1.06 g, 7.9 mmol) and dropwise with tert-butyl methyl ether (2 mL, over 5 minutes). The reaction is stirred for 1 hour at −20° C., warmed to 0° C. over 30 minutes, and stirred at 0° C. to 15° C. for 4 hours. The reaction is quenched by slow addition of 1N NaOH (2 mL) and then the reaction is filtered. The solids are washed with tert-butyl methyl ether and the phases of the filtrate are separated. The organic phase is dried over anhydrous magnesium sulfate, filtered and concentrated under vacuum. The residue is purified by column chromatography (silica gel, 20% ethyl acetate/hexane) to provide the title compound as a white foam (980 mg, 95%). $^1$H NMR (CDCl$_3$) δ7.5 (m, 6H), 7.3 (m, 9H), 5.79 (d, 1H), 5.14 (d, 1H), 4.5 (m, 1H), 4.4 (m, 1H), 2.2 (m, 1H), 1.42 (d, 1H); $^{13}$C NMR (CDCl$_3$) δ145.1, 136.2, 135.9, 129.0, 128.1, 127.3, 87.7, 77.4, 74.9, 43.2; IR (KBr) $v_{max}$ 3422, 3057, 1491, 1364, 1084, 1065, 1024 cm$^{-1}$.

EXAMPLE 28a

Preparation of cis-2-cyclopentenyl-1,4-diol.

A solution of (+/−)-cis-4-trityloxy-2-cyclopentenol (200 mg, 0.58 mmol, prepared in example 28) in ethanol (2 mL) is treated with p-toluenesulfonic acid (20 mg) and stirred at 55° C. for 8 hours. The reaction mixture is then concentrated under vacuum (55° C./15 mmHg) and the residue is purified by column chromatography (silica gel, 10% acetone/ethyl acetate) to provide the title compound (58 mg); cis/trans/1–2+1–4 addition, 30/1/trace.

EXAMPLE 29

Preparation of (+/−)-cis-3-tert-butyldimethylsilyloxycyclopentanol.

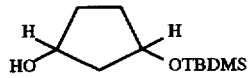

Combine (+/−)-cis-4-tert-butyldimethylsilyloxy-2-cyclopentenol (2.50 g, 11.6 mmol, prepared in example 3) and Ni$_2$B (8.5 mL of a 0.14M slurry in methanol, 10 mol %) in methanol (14 mL). Stir the slurry under an atmosphere of hydrogen for 18.5 hours. Then replace the hydrogen atmosphere with nitrogen, filter through diatomaceous earth and rinse the solids with methanol (50 mL). Concentrate the filtrate under vacuum (15 mmHg/40° C.) and purify the residue by Kugelrohr distillation (0.6 mmHg/60°–65° C.) to provide the title compound as a colorless oil (2.31 g, 92%).

EXAMPLE 30

Preparation of (1S,3R)-(−)-cis-3-tert-butyldimethylsilyloxycyclopentanol (A) and (1R,3S)-(+)-cis-3-tert-butyldimethylsilyloxycyclopentanyl acetate (B).

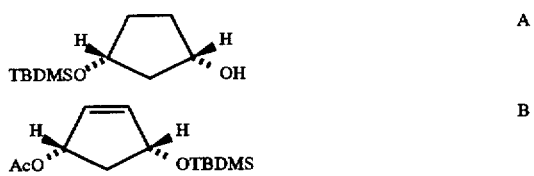

Scheme III, step A; Combine (+/−)-cis-3-tert-butyldimethylsilyloxycyclopentanol (2.119 g, 9.8 mmol, prepared in example 29), pancreatin (6.2 g, 3 weight equivalents), triethylamine (0.9 mL, 6.5 mmol) and vinyl acetate (4.3 mL) in tert-butyl methyl ether (12 mL) and stir for 27 hours at room temperature. Then filter the reaction through diatomaceous earth and concentrate the filtrate under vacuum (room temperature/15 mmHg). Purify the residue by column chromatography [silica gel, 55 g, hexane (300 mL) followed by 5% ethyl acetate/hexane (500 mL)] to provide the (1R,3S)-(+)-3-tert-butyldimethylsilyloxycyclopentanyl acetate (1.23 g, 49% yield, 98% ee as determined from gas chromatography with a chiral column) and (1S,3R)-(−)-3-tert-butyldimethylsilyloxycyclopentanol (771 mg, 37% yield, 92% ee as determined from its acetate derivative followed by GC chiral column analysis, see example 30a).

Physical data for (1Sr3R)-(−)-3-tert-butyldimethylsilyloxycyclopentanol; [α]$^{20}$$_D$=−3.7° (c=1.20, chloroform); $^1$H NMR (CDCl$_3$) δ4.4 (m, 1H), 4.3 (m, 1H), 3.03 (d, 1H), 1.9–1.6 (m, 6H), 0.89 (s, 9H), 0.07 (s, 6H); $^{13}$C NMR (CDCl$_3$) δ74.9, 74.1, 44.4, 34.2, 34.1, 25.8, 17.9, −4.9, −5.0; IR (neat) v$_{max}$ 3405, 2957, 2932, 2888, 2858, 1256, 1091, 1069, 1038, 1026 cm$^{-1}$.

Anal. calcd for C$_{11}$H$_{24}$O$_2$Si: C, 61.06; H, 11.18.
Found: C, 61.32; H, 11.13.

Physical data for (1R,3S)-(+)-3-tert-butyldimethylsilyloxycyclopentanyl acetate; [α]$^{20}$$_D$=+7.0° (c=1.12, chloroform).

Anal. calcd for C$_{13}$H$_{26}$O$_3$Si: C, 60.42; H, 10.14.
Found: C, 60.70; H, 10.51.

EXAMPLE 30a

Preparation of (1S,3R)-(−)-cis-3-tert-butyldimethylsilyloxycyclopentanyl acetate.

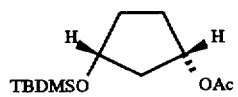

Combine (1S,3R)-(−)-cis-3-tert-butyldimethylsilyloxycyclopentanol (209 mg, 2.5 mmol, prepared in example 30), pyridine (1 mL), acetic anhydride (0.1 mL) and DMAP (5 mg). Stir the reaction at room temperature for 15.5 hours. Then dilute the reaction with diethyl ether (10 mL) and wash sequentially with 0.5M HCl ½ saturated with sodium chloride (2×10 mL), saturated sodium bicarbonate (10 mL) and brine (10 mL). Analysis of the filtrate indicates 92% ee for the title compound. Dry the organic phase over anhydrous magnesium sulfate, filter and concentrate under vacuum.

[α]$^{20}$$_D$=−6.6°(c=0.99, chloroform); $^1$H NMR (CDCl$_3$) δ5.0 (m, 1H), 4.2 (m, 1H), 2.2 (m, 1H), 2.02 (s, 3H), 1.9 (m, 1H), 1.7 (m, 2H), 0.89 (s, 9H), 0.05 (s, 3H), 0.04 (s, 3H); $^{13}$C NMR (CDCl$_3$) δ171.3, 75.0, 72.7, 42.3, 34.3, 30.5, 26.0, 21.5, 18.3, −4.5; IR (neat) v$_{max}$ 2957, 2932, 2859, 1740, 1250, 1115, 1096, 1045 cm$^{-1}$.

What is claimed is:

1. A process for preparing a CIS compound of the formula

formula (II)

wherein Pg is selected from the group consisting of benzyl, substituted benzyl, —CH$_2$OCH$_3$, —CH$_2$SCH$_3$, —OCH$_2$OCH$_2$phenyl, —CH$_2$OCH$_2$CH$_2$OCH$_3$, —CH$_2$OCH$_2$CCl$_3$, —CH(OCH$_2$CH$_2$CH$_3$)$_2$, —CH$_2$OCH$_2$CH$_2$Si(CH$_3$)$_3$, —CH(OC$_2$H$_5$)CH$_3$, —C(OCH$_3$)(CH$_3$)$_2$, —CH(CH$_3$)OCH(CH$_3$)$_2$—CH$_2$CCl$_3$, —C(CH$_3$)$_3$, —CH$_2$CH═CH$_2$, —CH$_2$CH═CHphenyl, —CH(phenyl)$_2$, —C(phenyl)$_3$, tetrahydropyranyl, 4-methoxytetrahydropyranyl, 3-bromotetrahydropyranyl, tetrahydrothiopyranyl, 4-methoxytetrahydrothiopyranyl, tetrahydrofuranyl, tetrahydrothiofuranyl, and SiR$_1$R$_2$R$_3$, wherein R$_1$, R$_2$ and R$_3$ are each independently C$_1$–C$_4$ alkyl, phenyl, benzyl, substituted phenyl or substituted benzyl, comprising;

a) dissolving a compound of the formula

formula (I)

wherein Pg is defined as above, in a suitable organic solvent; and b) treating the solution with a suitable Lewis acid and a suitable reducing agent at a temperature of from about −100° C. to about 20° C.

2. A process according to claim 1 wherein the suitable reducing agent is lithium aluminum hydride.

3. A process according to claim 2 wherein the suitable organic solvent is toluene/diethyl ether.

4. A process according to claim 2 wherein the suitable organic solvent is diethyl ether.

5. A process according to claim 2 wherein the suitable organic solvent is toluene/tert-butyl methyl ether.

6. A process as in either claim 2, claim 3 or claim 4 wherein the suitable Lewis acid is lithium iodide.

7. A process according to claim 6 wherein the mixture is cooled to a temperature of from about −78° C. to about −10° C.

8. A process according to claim 6 wherein the mixture is cooled to a temperature of about −25° C.

9. A process according to claim 8 wherein Pg is tert-butyldimethylsilyl.

10. A process for the preparation of the CIS enantiomer of the formula:

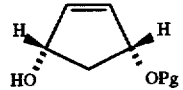

formula (IIa)

wherein Pg is selected from the group consisting of benzyl, substituted benzyl, —CH$_2$OCH$_3$, —CH$_2$SCH$_3$, —CH$_2$OCH$_2$phenyl, —CH$_2$OCH$_2$CH$_2$OCH$_3$, —CH$_2$OCH$_2$CCl$_3$, —CH(OCH$_2$CH$_2$Cl)$_2$, —CH$_2$OCH$_2$CH$_2$Si(CH$_3$)$_3$, —CH(OC$_2$H$_5$)CH$_3$, —C(OCH$_3$)(CH$_3$)$_2$, —CH(CH$_3$)OCH(CH$_3$)$_2$, —CH$_2$CCl$_3$, —C(CH$_3$)$_3$, —CH$_2$CH═CH$_2$, —CH$_2$CH═CHphenyl, —CH(phenyl)$_2$, —C(phenyl)$_3$, tetrahydropyranyl, 4-methoxytetrahydropyranyl, 3-bromotetrahydropyranyl, tetrahydrothiopyranyl, 4-methoxytetrahydrothiopyranyl, tetrahydrofuranyl, tetrahydrothiofuranyl, and SiR$_1$R$_2$R$_3$, wherein R$_1$, R$_2$ and R$_3$ are each independently C$_1$–C$_4$ alkyl, phenyl, benzyl, substituted phenyl or substituted benzyl, comprising;

a) dissolving an enantiomeric compound of the formula;

formula (Ia)

wherein Pg is defined as above, in a suitable organic solvent; and b) treating the solution with a suitable Lewis acid and a suitable reducing agent at a temperature of from about −100° C. to about 20° C.

11. A process for the preparation of the CIS enantiomer of the formula:

formula (IIb)

wherein Pg is selected from the group consisting of benzyl, substituted benzyl, —CH$_2$OCH$_3$, —CH$_2$SCH$_3$, —CH$_2$OCH$_2$phenyl, —CH$_2$OCH$_2$CH$_2$OCH$_3$, —CH$_2$OCH$_2$CCl$_3$, —CH(OCH$_2$CH$_2$Cl)$_2$, —CH$_2$OCH$_2$CH$_2$Si(CH$_3$)$_3$, —CH(OC$_2$H$_5$)CH$_3$, —C(OCH3)(CH$_3$)$_2$, —CH(CH$_3$)OCH(CH$_3$)$_2$, —CH$_2$CCl$_3$, —C(CH$_3$)$_3$, —CH$_2$CH=CH$_2$, —CH$_2$CH=CHphenyl, —CH(phenyl)$_2$, —C(phenyl)$_3$, tetrahydropyranyl, 4-methoxytetrahydropyranyl, 3-bromotetrahydropyranyl, tetrahydrothiopyranyl, 4-methoxytetrahydrothiopyranyl, tetrahydrofuranyl, tetrahydrothiofuranyl, and SiR$_1$R$_2$R$_3$, wherein R$_1$, R$_2$ and R$_3$ are each independently C$_1$–C$_4$ alkyl, phenyl, benzyl, substituted phenyl or substituted benzyl, comprising;

a) dissolving an enantiomeric compound of the formula; wherein Pg is defined as above, in a suitable organic solvent; and

formula (Ib)

b) treating the solution with a suitable Lewis acid and a suitable reducing agent at a temperature of from about −100° C. to about 20° C.

12. A process according to claim 1 wherein the suitable reducing agent is a 65+wt. % solution of sodium bis(2-methoxyethoxy)aluminum hydride in toluene.

* * * * *

UNITED STATES PATENT AND TRADEMARK OFFICE
CERTIFICATE OF CORRECTION

PATENT NO. : 5,728,899

DATED : March 17, 1998

INVENTOR(S) : Timothy T. Curren, David A. Hay, Jonathon C. Evans

Page 1 of 2

It is certified that error appears in the above-indentified patent and that said Letters Patent is hereby corrected as shown below:

Column 3, Line 49 reads "-$CH_2CH_2$phenyl" and should read --$CH_2OCH_2$phenyl--.

Column 5, Line 7 reads "halide", "hal" and should read --"halide", or "hal"--.

Column 17, Line 41 reads "dr" and should read --dt--.

Column 24, Line 14 reads "6 5.9" and should read --$\delta$ 5.9--.

Column 24, Line 17 reads "36" and should read --136--.

Column 24, Line 18 reads "907" and should read --2907--.

Column 29, Line 27 reads "columnar" and should read --column,--.

Column 30, Line 3 reads "(1Sr3R)" and should read --(1S,3R)--.

Column 30, Line 4 reads "methanesulfonyloxygyclopentyl" and should read --methanesulfonyloxycyclopentyl--.

Column 33, Line 66 reads "-$CH(OCH_2CH_2CH_3)_2$" and should read -- -$CH(OCH_2CH_2Cl)_2$--.

UNITED STATES PATENT AND TRADEMARK OFFICE
CERTIFICATE OF CORRECTION

PATENT NO. : 5,728,899
DATED : March 17, 1998
INVENTOR(S) : Timothy T. Curren, David A. Hay, Jonathon C. Evans It is certified that error appears in the above-indentified patent and that said Letters Patent is hereby corrected as shown below:

Column 35, Line 14 reads "-C(OCH3)" and should read -- -C(OCH$_3$)--.

Signed and Sealed this

Seventeenth Day of April, 2001

Attest:

NICHOLAS P. GODICI

Attesting Officer     Acting Director of the United States Patent and Trademark Office